(12) United States Patent
Kwon et al.

(10) Patent No.: US 11,581,067 B2
(45) Date of Patent: Feb. 14, 2023

(54) METHOD AND APPARATUS FOR GENERATING A CHEMICAL STRUCTURE USING A NEURAL NETWORK

(71) Applicants: SAMSUNG ELECTRONICS CO., LTD., Suwon-si (KR); RESEARCH & BUSINESS FOUNDATION SUNGKYUNKWAN UNIVERSITY, Suwon-si (KR)

(72) Inventors: Youngchun Kwon, Yongin-si (KR); Seokho Kang, Seoul (KR); Kyungdoc Kim, Seoul (KR); Jiho Yoo, Hwaseong-si (KR); Younsuk Choi, Seongnam-si (KR)

(73) Assignees: SAMSUNG ELECTRONICS CO., LTD., Suwon-si (KR); RESEARCH & BUSINESS FOUNDATION SUNGKYUNKWAN UNIVERSITY, Suwon-si (KR)

(*) Notice: Subject to any disclaimer, the term of this patent is extended or adjusted under 35 U.S.C. 154(b) by 1133 days.

(21) Appl. No.: 16/156,709

(22) Filed: Oct. 10, 2018

(65) Prior Publication Data

US 2019/0220573 A1     Jul. 18, 2019

(30) Foreign Application Priority Data

Jan. 17, 2018  (KR) ......................... 10-2018-0006275

(51) Int. Cl.
  *G16C 20/40*    (2019.01)
  *G06N 3/04*     (2006.01)
  (Continued)

(52) U.S. Cl.
  CPC ............... *G16C 20/40* (2019.02); *G06N 3/04* (2013.01); *G06N 3/0445* (2013.01);
  (Continued)

(58) Field of Classification Search
  CPC ........ G16C 20/40; G16C 20/00; G16C 20/50; G16C 20/70; G16C 20/80; G16C 99/00;
  (Continued)

(56) References Cited

U.S. PATENT DOCUMENTS

2003/0033088 A1   2/2003  Agrafiotis et al.
2005/0137807 A1   6/2005  Lippert et al.
  (Continued)

FOREIGN PATENT DOCUMENTS

JP     10-505832 A    6/1998
JP     2003-058579 A  2/2003
  (Continued)

OTHER PUBLICATIONS

Kristiadi ("Conditional Variational Autoencoder: Intuition and Implementation", Agustinus Kristiadi's Blog, Dec. 17, 2017) (Year: 2017).*

(Continued)

*Primary Examiner* — Daniel R Miller
*Assistant Examiner* — Christian T Bryant
(74) *Attorney, Agent, or Firm* — Sughrue Mion, PLLC

(57) ABSTRACT

A method of generating a chemical structure performed by a neural network device includes receiving a target property value and a target structure characteristic value; selecting first generation descriptors; generating second generation descriptors; determining, using a first neural network of the neural network device, property values of the second generation descriptors; determining, using a second neural network of the neural network device, structure characteristic values of the second generation descriptors; selecting, from the second generation descriptors, candidate descriptors that satisfy the target property value and the target structure characteristic value; and generating, using the second neural (Continued)

network of the neural network device, chemical structures for the selected candidate descriptors.

26 Claims, 13 Drawing Sheets

(51) Int. Cl.

| | | |
|---|---|---|
| *G06N 3/08* | (2006.01) | |
| *G16C 20/80* | (2019.01) | |
| *G16C 20/50* | (2019.01) | |
| *G16C 20/70* | (2019.01) | |
| *G16C 20/00* | (2019.01) | |
| *G06N 3/06* | (2006.01) | |
| *G16C 99/00* | (2019.01) | |
| *G06N 3/02* | (2006.01) | |
| *G16C 60/00* | (2019.01) | |
| *G16B 15/00* | (2019.01) | |
| *G01N 37/00* | (2006.01) | |
| *G16C 20/20* | (2019.01) | |
| *G16C 20/30* | (2019.01) | |
| *G06N 3/12* | (2006.01) | |
| *G06N 3/126* | (2023.01) | |

(52) U.S. Cl.
CPC ......... *G06N 3/0454* (2013.01); *G06N 3/0472* (2013.01); *G06N 3/06* (2013.01); *G06N 3/08* (2013.01); *G06N 3/126* (2013.01); *G16C 20/00* (2019.02); *G16C 20/50* (2019.02); *G16C 20/70* (2019.02); *G16C 20/80* (2019.02); *G01N 37/00* (2013.01); *G06N 3/02* (2013.01); *G16B 15/00* (2019.02); *G16C 20/20* (2019.02); *G16C 20/30* (2019.02); *G16C 60/00* (2019.02); *G16C 99/00* (2019.02)

(58) Field of Classification Search
CPC ........ G16C 60/00; G16C 20/30; G16C 20/20; G06N 3/04; G06N 3/0445; G06N 3/0454; G06N 3/0472; G06N 3/08; G06N 3/126; G06N 3/06; G06N 3/02; G06N 20/00; G16B 15/00; G01N 37/00
See application file for complete search history.

(56) References Cited

U.S. PATENT DOCUMENTS

| | | |
|---|---|---|
| 2017/0124482 A1 | 5/2017 | Yoo et al. |
| 2017/0193200 A1 | 7/2017 | Hsu et al. |
| 2018/0032663 A1 | 2/2018 | Yoo et al. |

FOREIGN PATENT DOCUMENTS

| | | |
|---|---|---|
| JP | 2004-301928 A | 10/2004 |
| JP | 2006-113893 A | 4/2006 |
| KR | 10-2012-0085178 A | 7/2012 |
| KR | 10-2017-0052344 A | 5/2017 |
| KR | 10-2018-0014471 A | 2/2018 |

OTHER PUBLICATIONS

Liu et al. (Materials discovery and design using machine learning, Journal of Materiomics, vol. 3, Issue 3, 2017, pp. 159-177, ISSN 2352-8478, https://doi.org/10.1016/j.jmat.2017.08.002.) (Year: 2017).*

Pyzer-Knappp et al. ("What Is High-Throughput Virtual Screening? A Perspective from Organic Materials Discovery", Annual Review of Materials Research 2015, vol. 45:195-216, 2015, https://doi.org/10.1146/annurev-matsci-070214-020823) (Year: 2015).*

Yu ("Natural Product-Like Virtual Libraries: Recursive Atom-Based Enumeration", J. Chem. Inf. Model. 2011, 51, 3, 541-557, Publication Date: Mar. 9, 2011 ,https://doi.org/10.1021/ci1002087) (Year: 2011).*

Varnek et al. ("Machine Learning Methods for Property Prediction in Chemoinformatics: Quo Vadis?", J. Chem. Inf. Model. 2012, 52, 6, 1413-1437, Publication Date: May 14, 2012, https://doi.org/10.1021/ci200409x) (Year: 2012).*

Kusner et al. ("Grammar variational autoencoder". arXiv:1703.01925 [stat.ML], Mar. 6, 2017) (Year: 2017).*

Communication dated Jun. 6, 2019, issued by the European Patent Office in counterpart European Application No. 18201299.7.

Gomez-Bombarelli, et al., "Automatic Chemical Design Using a Data-Driven Continuous Representation of Molecules", Jan. 12, 2018, ACS Central Science, vol. 4, No. 2, XP055589835, p. 268-276, 9 pages total.

Blaschke, et al., "Application of generatie autoencoder in de novo molecular design", Nov. 21, 2017, Arxiv.org, XP080839053, 13 pages total.

* cited by examiner

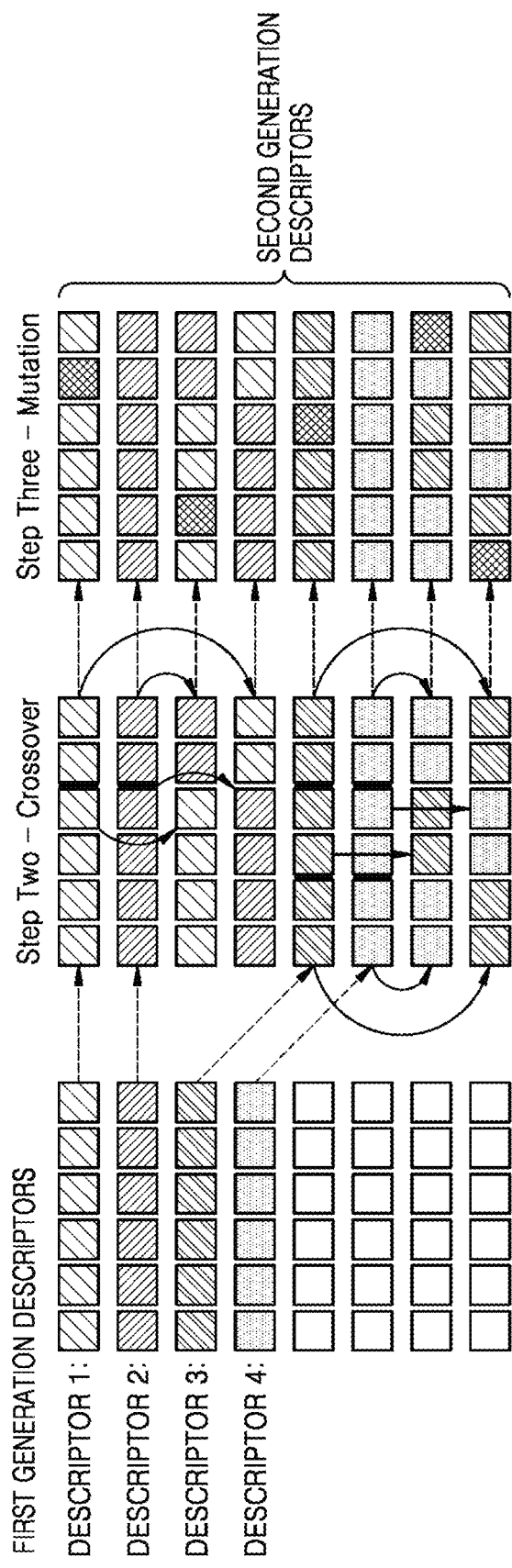

METHOD AND APPARATUS FOR GENERATING A CHEMICAL STRUCTURE USING A NEURAL NETWORK

CROSS-REFERENCE TO RELATED APPLICATION

This application claims priority from Korean Patent Application No. 10-2018-0006275, filed on Jan. 17, 2018, in the Korean Intellectual Property Office, the disclosure of which is incorporated herein by reference in its entirety.

BACKGROUND

1. Field

The present disclosure relates to methods and apparatuses for generating a chemical structure using a neural network.

2. Description of the Related Art

A neural network refers to a computational architecture that models a biological brain. With the advancement of neural network technologies, various types of electronic systems have analyzed input data and extracted valid information by using neural networks.

In recent years, extensive research has been conducted into methods of selecting chemical structures to be used in material development by evaluating properties of the chemical structures using the neural network technologies. Particularly, there is a need to generate new chemical structures satisfying a variety of requirements by using the neural network technologies.

However, techniques for generating chemical structures are often inefficient, error-prone, computationally intensive, and/or incapable of accurately generating chemical structures that satisfy various metrics or incapable of generating chemical structures entirely.

SUMMARY

Provided are methods and apparatuses for generating a chemical structure using a neural network. Also, provided are computer-readable media including a program, which when executed by a computer, performs the methods. The present disclosure may address the technical problems addressed above and/or other technical problems not addressed above. As an example, some implementations herein permit a neural network device to generate chemical structures that satisfy various requirements (e.g., a target property value and a target structure characteristic value). Further, and continuing the example, the neural network device may employ a set of models (e.g., a deep neural network, a recurrent neural network, a conditional variational autoencoder, and/or the like) that permits the neural network device to generate chemical structures that satisfy various input requirements. In this way, some implementations herein permit the neural network device to address the technical shortcomings of the related systems, and/or permit the neural network device to generate chemical structures in a more accurate manner, in a more efficient manner, and/or in a manner that conserves computing resources as compared to other systems and techniques that are incapable of doing so.

Additional aspects will be set forth in part in the description which follows and, in part, will be apparent from the description, or may be learned by practice of the presented exemplary embodiments.

According to an aspect of an exemplary embodiment, a method of generating a chemical structure performed by a neural network device includes receiving a target property value and a target structure characteristic value; selecting first generation descriptors based on the target property value and the target structure characteristic value; generating second generation descriptors based on the first generation descriptors; determining, using a first neural network of the neural network device, property values of the second generation descriptors; determining, using a second neural network of the neural network device, structure characteristic values of the second generation descriptors; selecting, from the second generation descriptors, candidate descriptors that satisfy the target property value and the target structure characteristic value, the selecting of the candidate descriptors being based on determining the property values and based on determining the structure characteristic values; and generating, using the second neural network of the neural network device, chemical structures for the selected candidate descriptors.

According to an aspect of another exemplary embodiment, a neural network device configured to generate a chemical structure includes a user interface configured to receive a target property value and a target structure characteristic value; a memory configured to store at least one program; and a processor configured to execute the at least one program to: select first generation descriptors based on the target property value and the target structure characteristic value; generate second generation descriptors based on the first generation descriptors; determine, using a first neural network, property values of the second generation descriptors; determine, using a second neural network, structure characteristic values of the second generation descriptors; select, from the second generation descriptors, candidate descriptors that satisfy the target property value and the target structure characteristic value based on determining the property values and the structure characteristic values; and generate, using the second neural network, chemical structures for the selected candidate descriptors.

According to an aspect of another exemplary embodiment, a method of generating a chemical structure by using a conditional variational autoencoder (CVAE) of a neural network device includes converting first descriptors into low-dimensional latent variables; mapping the low-dimensional latent variables to a latent map; selecting, using the latent map, a region to which the low-dimensional latent variables that are converted from the first descriptors are not mapped; converting latent variables of the selected region into high-dimensional second descriptors; and generating chemical structures for the second descriptors.

According to an aspect of another exemplary embodiment, a neural network device configured to generate a chemical structure by using a conditional variational autoencoder (CVAE) includes a memory configured to store at least one program; and a processor configured to execute the at least one program to: convert first descriptors into low-dimensional latent variables; map the low-dimensional latent variables to a latent map; select, using the map, a region to which the low-dimensional latent variables converted from the first descriptors are not mapped; and convert latent variables of the selected region into high-dimensional second descriptors; and generate chemical structures for the high-dimensional second descriptors.

According to an aspect of another exemplary embodiment, a non-transitory computer-readable recording medium includes one or more instructions, which when executed by one or more processors, causes the one or more processors to perform operations associated with an exemplary embodiment.

BRIEF DESCRIPTION OF THE DRAWINGS

These and/or other aspects will become apparent and more readily appreciated from the following description of the exemplary embodiments, taken in conjunction with the accompanying drawings in which:

FIG. 8 is a diagram for describing a process of applying a genetic algorithm to the first generation descriptors according to an exemplary embodiment;

DETAILED DESCRIPTION

Figure 1:
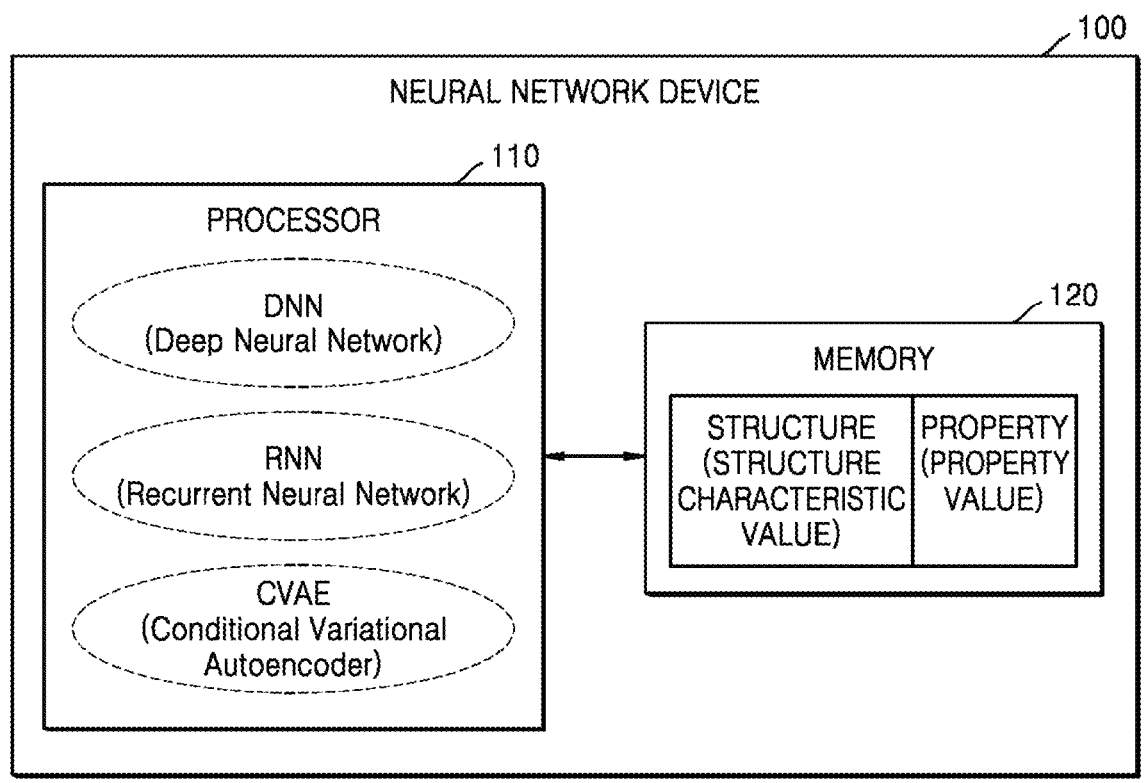
FIG. 1 is a block diagram illustrating a hardware configuration of a neural network device according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The terms "according to some exemplary embodiments" or "according to an exemplary embodiment" used throughout the specification do not necessarily indicate the same exemplary embodiment.

Some exemplary embodiments of the present disclosure may be represented by functional block configurations and various processing operations. Some or all of these functional blocks may be implemented using various numbers of hardware and/or software components that perform particular functions. For example, the functional blocks of the present disclosure may be implemented using one or more microprocessors or circuits for a given function. Also, for example, the functional blocks of the present disclosure may be implemented in various programming or scripting languages. The functional blocks may be implemented with algorithms running on one or more processors. The present disclosure may also employ conventional techniques for electronic configuration, signal processing, and/or data processing. The terms "mechanism", "element", "unit" and "configuration" may be used in a broad sense and are not limited to mechanical and physical configurations, and may be implemented in hardware, firmware, software, and/or a combination thereof.

Also, connection lines or connection members between the components illustrated in the drawings are merely illustrative of functional connections and/or physical or circuit connections. In actual devices, connections between the components may be represented by various functional connections, physical connections, or circuit connections that may be replaced or added.

Meanwhile, with respect to the terms used herein, a descriptor that is data used in a neural network system refers to an indicator value used to describe characteristics of a substance and may be acquired by performing a relatively simple computation on a given substance. According to an exemplary embodiment, a descriptor may include a molecular structure fingerprint indicating whether or not a substance includes a particular partial structure (e.g., Morgan fingerprint and extended connectivity fingerprint (ECFP)) and a quantitative structure-property relationship (QSPR) configured with a value that may immediately be calculated such as a molecular weight or the number of a partial structure (e.g., ring) included in a molecular structure.

In addition, a property refers to a characteristic possessed by a substance and may be a real number measured by an experiment or calculated by a simulation. For example, when the substance is a display material, the property may be a transmission wavelength, emission wavelength, or the like with respect to light. When the substance is a battery material, the property may be a voltage. Unlike the descriptor, calculation of the property may require more complex simulations and require more time.

Also, a structure refers to an atomic level structure of a substance. In order to derive a property by performing First Principles Calculation, the structure should be expressed at an atomic level. Thus, a structure of a substance should be derived to an atomic level to generate a novel chemical structure. The structure may be a structural formula based on atomic bonding relationships or a character string in a simple format (one-dimensional). The format of the character string expressing the structure may be a Simplified Molecular-input Line-entry System (SMILES) code, a Smiles Arbitrary Target Specification (SMARTS) code, an International Chemical Identifier (InChi) code, or the like.

In addition, a factor refers to an element defining the relationships among the descriptor, the property, and the structure. The factor may be determined by machine learning based on a descriptor-property-structural formula stored in a database. Thus, the way in which the factor is related to the descriptor, the property, and the structural formula may be determined.

Hereinafter, exemplary embodiments of the present disclosure will be described in detail with reference to the accompanying drawings.

FIG. 1 is a block diagram illustrating a hardware configuration of a neural network device according to an exemplary embodiment.

A neural network device 100 may be implemented using various types of devices such as a personal computer (PC), a server device, a mobile device, and an embedded device. Examples of the neural network device 100 may include, but are not limited to, a smartphone, a tablet device, an augmented reality (AR) device, an Internet of Things (IoT) device, an autonomous vehicle, a robot, a medical device, and the like which perform speech recognition, image recognition, image classification, and the like using a neural network. Furthermore, the neural network device 100 may be a dedicated hardware (HW) accelerator mounted on the devices described above. The neural network device 100 may be a hardware accelerator such as a neural processing unit (NPU), a tensor processing unit (TPU), and a neural engine, which are dedicated modules for driving a neural network, without being limited thereto.

Referring to FIG. 1, the neural network device 100 includes a processor 110 and a memory 120. FIG. 1 illustrates components of the neural network device 100 related to the exemplary embodiments of the present disclosure. Thus, it should be apparent to a person skilled in the art that the neural network device 100 may further include any other components in addition to the components shown in FIG. 1.

The processor 110 controls the overall function for driving the neural network device 100. For example, the processor 110 controls the overall operation of the neural network device 100 by executing programs stored in the memory 120 of the neural network device 100. The processor 110 may be implemented as a central processing unit (CPU), a graphics processing unit (GPU), an application processor (APU), and the like provided in the neural network device 100, without being limited thereto.

The memory 120 is a component, at least partially implemented in hardware, that stores a variety of data processed by the neural network device 100. For example, the memory 120 may store data to be processed by the neural network device 100. The memory 120 may also store applications, drivers, and the like to be driven by the neural network device 100. The memory 120 may include random access memory (RAM) such as dynamic random access memory (DRAM) and static random access memory (SRAM), read-only memory (ROM), electrically erasable programmable read-only memory (EEPROM), CD-ROM, Blue-ray, optical disk storage, hard disk drive (HDD), solid state drive (SSD), flash memory, or the like.

Meanwhile, the memory 120 stores a structure characteristic value and a property value that are associated with each other as one set. The neural network device 100 may read the structure characteristic value and the property value from the memory 120 or write the structure characteristic value and the property value in the memory 120. The property value refers to a characteristic of a substance and may be a real number measured by an experiment or calculated by a simulation. In addition, the structure characteristic value refers to an indicator value used to express a structure of a substance and may be a molecular structure fingerprint indicating whether or not the substance includes a particular partial structure (e.g., Morgan fingerprint and ECFP).

The processor 110 may drive a deep neural network (DNN), a recurrent neural network (RNN), and a conditional variational autoencoder (CVAE).

The processor 110 may allow the DNN to learn by using descriptors and properties (property values) and may determine a factor defining the relationship between the descriptors and the properties in this process. By driving the trained DNN, the processor 110 may perform a computation using a descriptor as input data to an input layer and generate a property value as output data based on a computation result.

The processor 110 may allow the RNN to learn by using descriptors and structures (structure characteristic values) and may determine a factor defining the relationship between the descriptors and the structures in this process. By driving the trained RNN, the processor 110 may perform a computation using a descriptor or a factor as input data to an input layer and generate a structure characteristic value as output data based on a computation result.

The processor 110 may generate a new chemical structure that is not present in the database by using the CVAE. Particularly, a descriptor, which is high-dimensional data stored in the database, may be used as input data to an input layer of the CVAE and encoding by converting the high-dimensional descriptor into a latent variable, which is low-dimensional data, may be performed by an encoder. Next, the low-dimensional latent variable is decoded by a decoder of the CVAE. Finally, a descriptor, which is high-dimensional data corresponding to a new chemical structure, may be output from an output layer.

Meanwhile, the neural network device 100 may further include a user interface (not shown). The user interface refers to a device used to input data to control the neural network device 100. Examples of the user interface may include, but are not limited to, a key pad, a dome switch, a touch pad (e.g., capacitive overlay type, resistive overlay type, infrared beam type, surface acoustic wave type, integral strain gauge type, and piezo electric type), a jog wheel, and a jog switch.

Hereinafter, methods of generating a chemical structure by using the neural network device 100 and evaluating the generated chemical structure will be described in detail. The methods to be described below may be performed by the processor 110 and the memory 120 of the neural network device 100.

Figure 2:
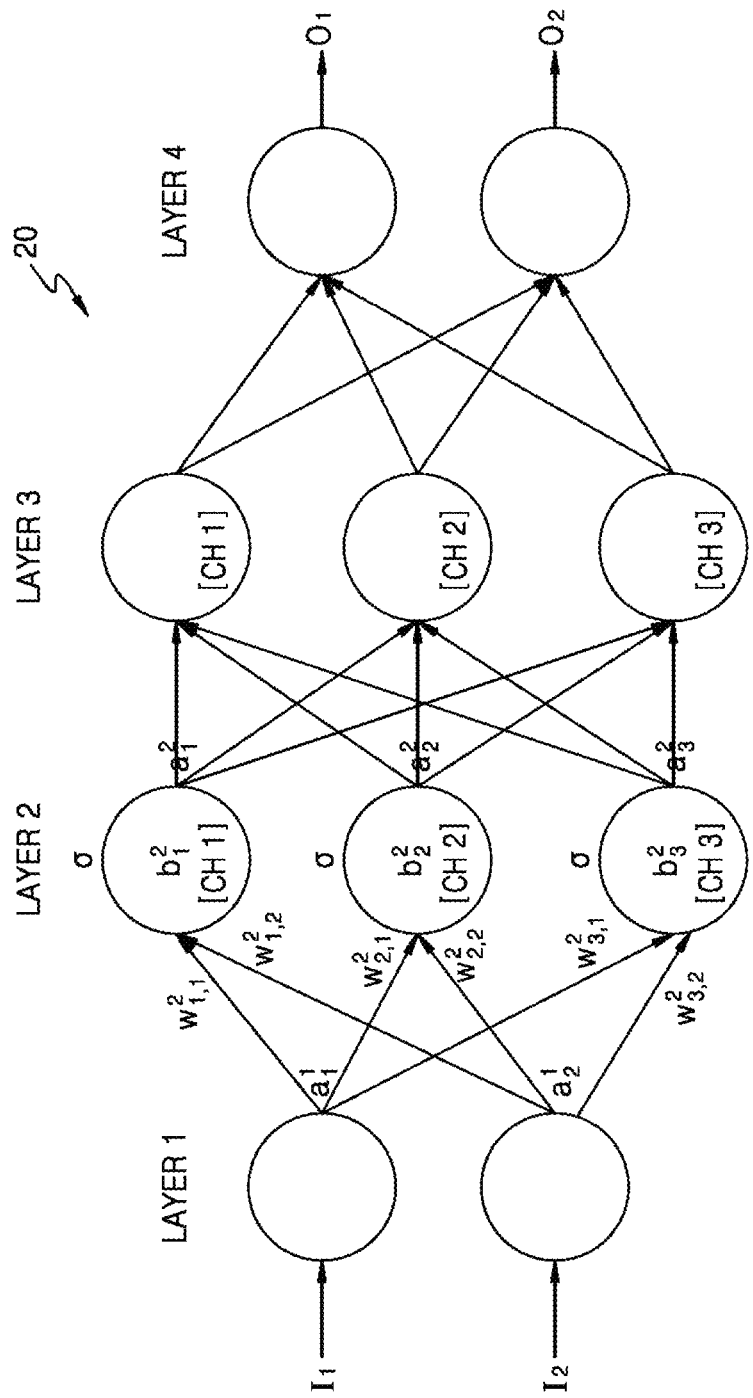
FIG. 2 is a diagram for describing a computation performed by a deep neural network (DNN) according to an exemplary embodiment.

FIG. 2 is a diagram for describing a computation performed by a DNN according to an exemplary embodiment.

Referring to FIG. 2, a DNN 20 has a structure including an input layer, one or more hidden layers, and an output layer. Further, the DNN 20 performs a computation based on received input data (e.g., $I_1$ and $I_2$), and generates output data (e.g., $O_1$ and $O_2$) based on a computation result.

For example, as illustrated in FIG. 2, the DNN 20 may include an input layer (Layer 1), two hidden layers (Layer 2 and Layer 3), and an output layer (Layer 4). Since the DNN 20 may include many layers to process valid information, the DNN 20 may process more complex data as compared to a neural network including a single layer. Meanwhile, although the DNN 20 illustrated in FIG. 2 includes 4 layers, the DNN 20 is merely an example and may also include more or less layers and more or less channels than those illustrated in FIG. 2. That is, the DNN 20 may have various structures of layers different from that illustrated in FIG. 2.

Each of the layers included in the DNN 20 may have a plurality of channels. The channels may correspond to a plurality of artificial nodes known as neurons, processing elements (PEs), units, or similar terms. For example, as illustrated in FIG. 2, Layer 1 may include two channels (nodes), and Layers 2 and 3 may include three channels, respectively. However, the layers are merely examples and each of the layers included in the DNN 20 may have various numbers of channels (nodes).

The channels included in each of the layers of the DNN 20 may be interconnected to process data. For example, a channel may perform a computation of data received from channels of one layer and output a computation result to channels of another layer.

Input and output of each channel may be referred to as input activation and output activation. That is, an activation may be not only an output of one channel but also a parameter corresponding to an input of channels included in a successive layer. Meanwhile, each of the channels may determine an activation thereof based on activations and weights received from channels included in a previous layer. The weight is a parameter used to calculate the output activation of each channel and may be a value assigned to the relationship between channels.

Each of the channels may be processed by a computational unit or a processing element that receives an input and outputs an output activation. The input-output of each channel may be mapped. For example, when σ is an activation function, $w_{jk}^i$ is a weight from a $k^{th}$ channel included in an $(i-1)^{th}$ layer to a $j^{th}$ channel included in an $i^{th}$ layer, $b_j^i$ is a bias of the $j^{th}$ channel included in the $i^{th}$ layer, and $a_j^i$ is an activation of the $j^{th}$ channel of the $i^{th}$ layer, an activation $a_j^i$ may be calculated using Expression 1 below.

$$a_j^i = \sigma\left(\sum_k (w_{jk}^i \times a_k^{i-1}) + b_j^i\right) \qquad \text{Expression 1}$$

As illustrated in FIG. 2, an activation of a first channel (CH1) of a second layer (Layer 2) may be expressed as $a_1^2$. In addition, $a_1^2$ may have a value of $a_1^2=\sigma(w_{1,1}^2 \times a_1^1 + w_{1,2}^2 \times a_2^1 + b_1^2)$ according to Expression 1. However, the above-described Expression 1 is merely an example for describing the activation and the weight used to process data in the DNN 20 and the exemplary embodiment is not limited thereto. The activation may be a value obtained by inputting a sum of activations received from the previous layer to an activation function and processing the result with a rectified linear unit (ReLU).

According to an exemplary embodiment, the DNN 20 may determine a factor defining the relationship between a descriptor and a property via learning using descriptors and property values. That is, among Layers 1 to 4 constituting the DNN 20, the descriptor corresponds to the input layer (Layer 1), the property value corresponds to the output layer (Layer 4), and the factor corresponds to at least one hidden layer (Layers 2 and 3).

The DNN 20 may perform a computation using the descriptor as input data to the input layer and generate the property value as output data based on a computation result.

Figure 3:
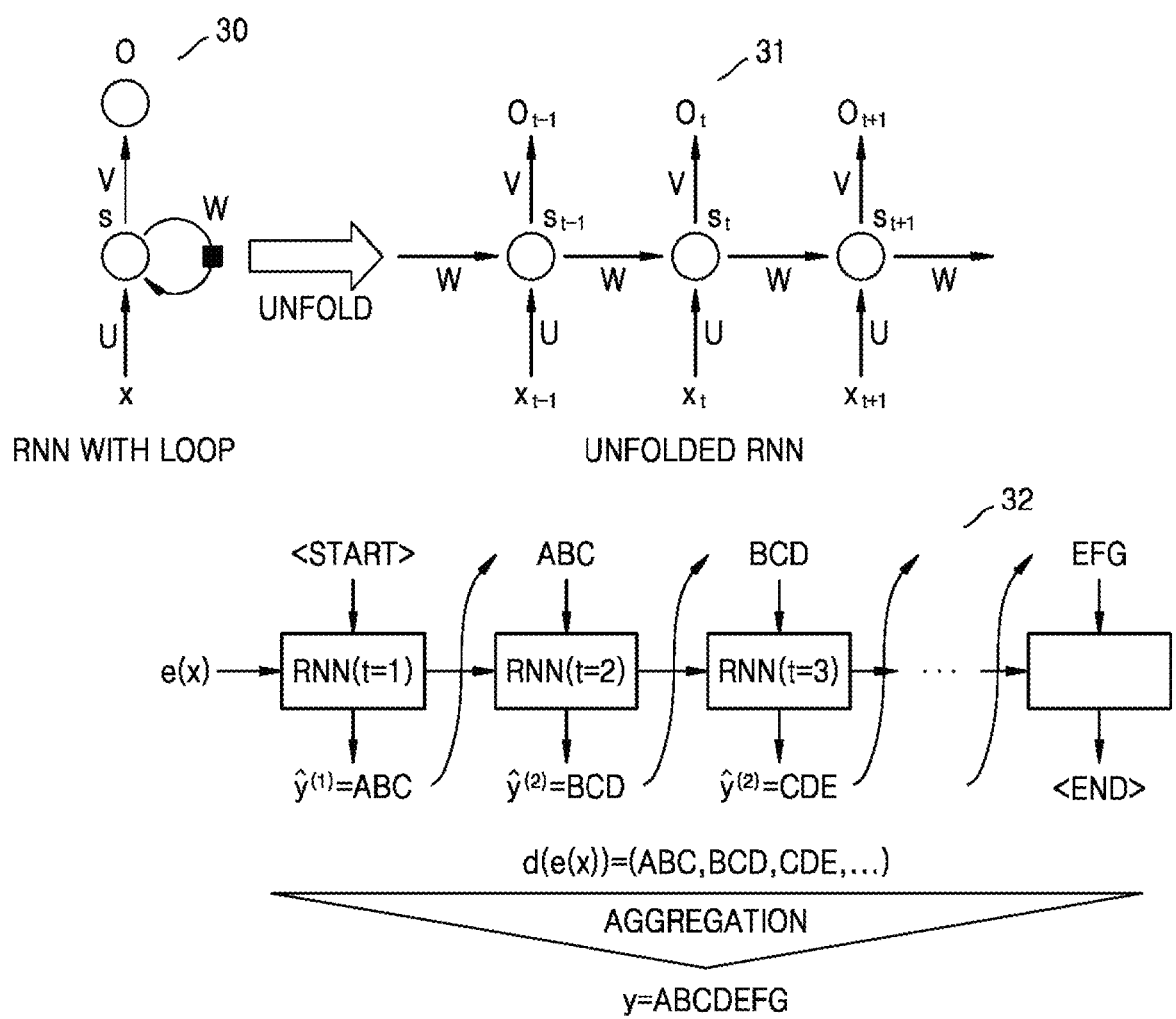
FIG. 3 is a diagram for describing a computation performed by a recurrent neural network (RNN) according to an exemplary embodiment.

FIG. 3 is a diagram for describing a computation performed by an RNN according to an exemplary embodiment.

Hereinafter, descriptions given above with reference to FIG. 2 will not be repeated for descriptive convenience.

An RNN 30 is a neural network that learns using data changing with time such as time-series data, and the RNN 30 is constructed by connecting a network between a reference time point t and a next time point t+1. That is, the RNN 30 is a neural network in which a temporal aspect is considered and is capable of effectively learning a pattern from data sequentially input or data input with a sequence of features by modifying a model to allow a recursive input to a hidden layer of the neural network.

Referring to FIG. 3, nodes s constituting a hidden layer of the RNN 30 are illustrated. The nodes s may perform a computation based on input data x and generate output data o. The RNN 30 may apply the same task to all sequences and a final output result of the node s is affected by a result of a previous calculation.

An RNN 31 is an unfolded RNN 30 with a loop. The term "unfold" the RNN 30 refers to expressing the RNN 30 for the entire sequence. In the RNN 31, $x_t$ is an input value at a time step t, and $s_t$ is a hidden state at the time step t. The $s_t$ may be expressed by Expression 2 below. In Expression 2, a tan h or Relu function may be used as function f. The $s_{-1}$ to calculate a first hidden state may generally be initialized to 0. In addition, in the RNN 31, $o_t$ is an output value at the time step t.

$$s_t = f(Ux_t + Ws_{t-1}) \qquad \text{Expression 2}$$

Here, $s_t$ is a memory portion of the network and stores information on events at previous time steps. The output value $o_t$ depends only on the memory of the current time step t.

Meanwhile, as compared to the existing neural network structure in which the parameters are different from each other, the RNN 31 shares the parameters U, V, and W for all time steps. That is, since each step of the RNN 31 performs almost the same calculation except for an input value, the number of parameters to be learned may be reduced.

According to an exemplary embodiment, an RNN 32 may determine a factor defining the relationship between the descriptor and the structure via learning using the descriptors and the structures (structure characteristic values). As described above with reference to FIG. 2, the factor may be at least one hidden layer. The RNN 32 may perform a computation using a descriptor or a factor as input data to the input layer and generate a structure characteristic value as output data based on a computation result.

For example, when a character string representing the structure characteristic value is "ABCDEFG", input and output of each time step may be "ABC", "BCD", "CDE", "DEF", and "EFG". That is, each step of the RNN 32 may use a next character string of a character string input at a time point t as input of a time point t+1.

The RNN 32 may perform learning to maximize the probability of generating a character string representing a structure s for data h and s (i.e., the factor and structure data). The probability p of generating a character string may be expressed by Expression 3 below.

$$p(y|e(x)) = \prod_{t=1}^{T} p(y^{(t)}|e(x), y^{(1)}, \ldots, y^{(t-1)}) \qquad \text{Expression 3}$$

When the construction of the RNN portion is completed by learning (i.e., when parameters of an RNN model used to determine a structure factor is determined), the factor obtained by encoding the descriptor may be decoded. According to another exemplary embodiment, decoding proceeds sequentially by acquiring a first part 'ABC' of a decoded character string by using a factor e(x) as an input, acquiring a part 'BCD' of the character string using the acquired part 'ABC' as an input, and acquiring a part 'CED' of the character string using the acquired part 'BCD'.

Referring to FIG. 3, the first two characters of the part of the character string at the time point t are the same last two characters of the part of the character string at a time point t−1. Then, characters of each time point are aggregated to output a single character string "ABCDEFG."

Figure 4:
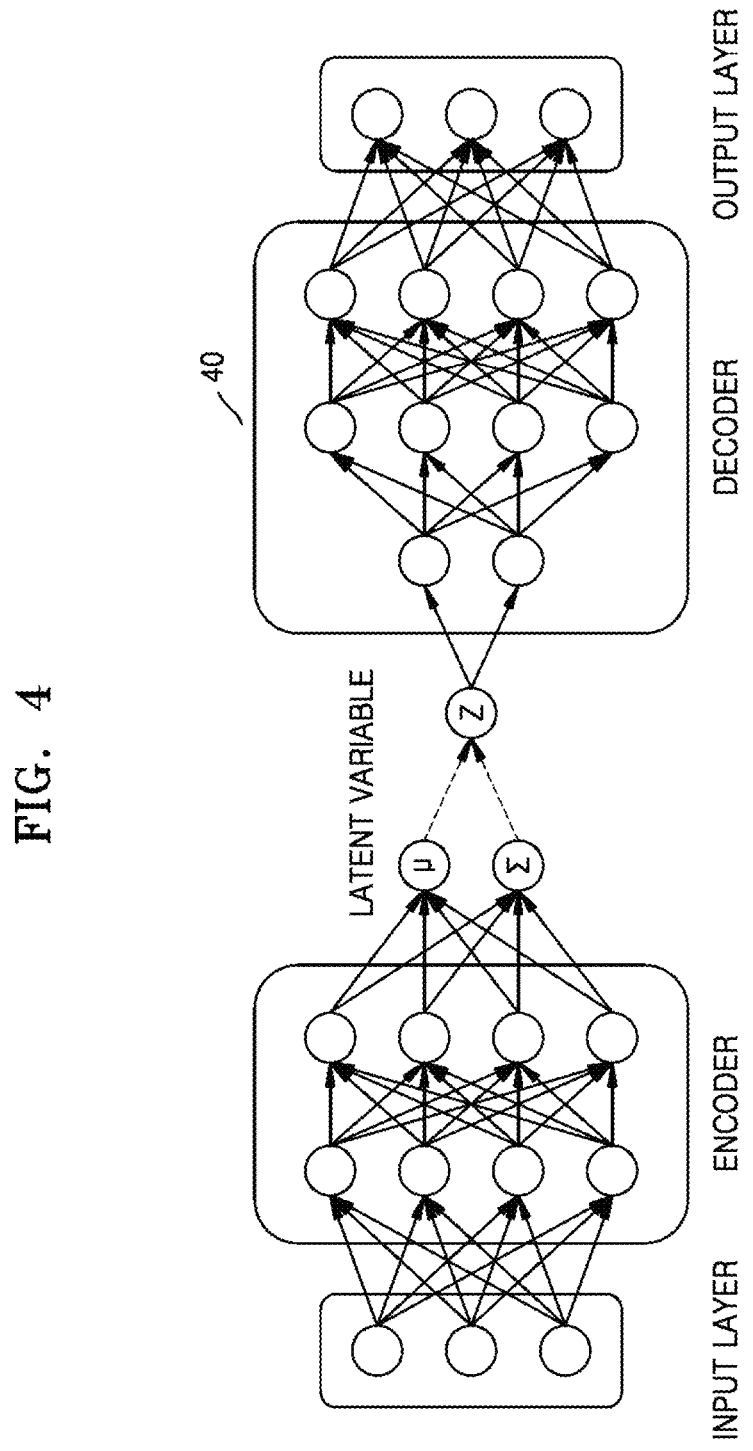
FIG. 4 is a diagram for describing a computation performed by a conditional variational autoencoder (CVAE) according to an exemplary embodiment.

FIG. 4 is a diagram for describing a computation performed by a CVAE according to an exemplary embodiment.

Referring to FIG. 4, a CVAE 40 has a structure including an input layer, an encoder, a decoder, and an output layer. High-dimensional data such as an image stored in a database is used as input data to the input layer of the CVAE 40, and the encoder performs encoding by converting the high-dimensional data into a low-dimensional latent variable z. According to an exemplary embodiment, the latent variable z follows a normal distribution with a mean µ and a variance σ and may be, for example, two-dimensional to fifty-dimensional data. Then, the decoder decodes the low-dimensional latent variable z to output a new image (high-dimensional data) that is not present in the database from the output layer.

For example, when an image of a human shape is used as input data, the latent variable may be a shape of an object, a view point of a camera, information on a light source, and the like. When an image of a number is used as input data, the latent variable may be an angle between lines, an aspect ratio, and the like.

Meanwhile, the latent variable z may be mapped to a latent map. When a predetermined value z' included in a region of the latent map to which the latent variable z is not mapped is input to the decoder, new data that is not stored in the database may be generated from the output layer.

In the CVAE 40, a descriptor that is high-dimensional data stored in the database may be used as input data to the input layer and encoding by converting the high-dimensional descriptor into a low-dimensional latent variable may be performed by the encoder. Then, the low-dimensional latent variable may be decoded by the decoder of the CVAE 40. Finally, a descriptor, which is high-dimensional data corresponding to a new chemical structure, may be output from the output layer.

Figure 5:
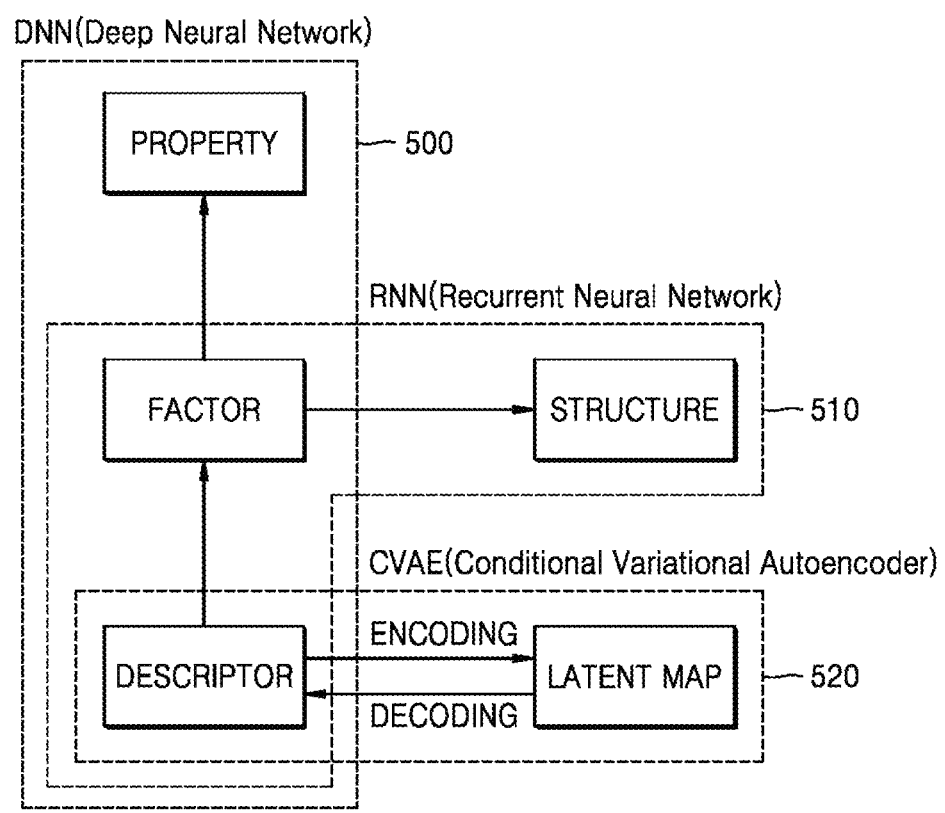
FIG. 5 is a conceptual diagram illustrating a neural network system to generate a chemical structure according to an exemplary embodiment.

FIG. 5 is a conceptual diagram illustrating a neural network system to generate a chemical structure according to an exemplary embodiment.

Referring to FIG. 5, a neural network system configured to generate a chemical structure by using a DNN 500, an RNN 510, and a CVAE 520 is illustrated.

The descriptor, as data used in the neural network system, may include a QSPR descriptor configured with an immediately calculable value such as a molecular structure fingerprint indicating whether or not a particular partial structure (ECFP) is included in a substance. The property refers to a characteristic possessed by a substance and may be a real number measured by an experiment or calculated by a simulation. The structure refers to an atomic level structure of a substance. A character string format expressing the structure may be a SMILES code, a SMARTS code, an InChi code, or the like. For example, a structural formula may be expressed by a SMILES code as shown in Expression 4 or by a SMARTS code as shown in Expression 5.

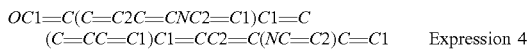

OC1=C(C=C2C=CNC2=C1)C1=C
(C=CC=C1)C1=CC2=C(NC=C2)C=C1     Expression 4

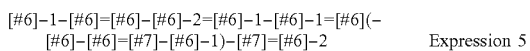

[#6]-1-[#6]=[#6]-[#6]-2=[#6]-1-[#6]-1=[#6](-
[#6]-[#6]=[#7]-[#6]-1)-[#7]=[#6]-2     Expression 5

The factor is an element defining the relationships among the descriptor, the property, and the structure. The factor may be at least one hidden layer. When the factor includes a plurality of hidden layers, a factor defining the relationship between the descriptor and the property, a factor defining the relationship between the descriptor and the structure, and the like may be determined for each hidden layer.

The latent map refers to visualizable coordinates to which two-dimensionally or three-dimensionally expressed descriptors are mapped. Similarity between the descriptors may be visualized and identified by using the latent map.

The DNN 500 may perform a computation using a descriptor as input data to the input layer and generate a property (property value) as output data based on a computation result. The RNN 510 may perform a computation using a descriptor or a factor as input data to the input layer and generate a structure (structure characteristic value) as output data based on a computation result. As a character string format expressing the structure characteristic value, the SMILES code, the SMARTS code, or the like may be used.

In addition, the DNN 500 and the RNN 510 may determine factors defining the relationship among the descriptor, the property, and the structure by performing learning based on the relationship between the property (property value) and the structure (structure characteristic value) stored in the memory. According to an exemplary embodiment, the factor may be at least one hidden layer. When the factor includes a plurality of hidden layers, a factor defining the relationship between the descriptor and the property and a factor defining the relationship between the descriptor and the structure may be determined for each hidden layer.

The RNN 510 may perform the computation using the factor determined by the DNN 500 as input data to the input layer and generate the structure characteristic value as output data based on the computation result.

In the CVAE 520, a descriptor, which is high-dimensional data stored in the database, is used as input data to an input layer and encoding by converting the high-dimensional descriptor into a latent variable, which is low-dimensional data, may be performed by an encoder. Then, when the decoder of the CVAE 520 decodes the low-dimensional latent variable, a descriptor which is high-dimensional data corresponding to a new chemical structure may be output from an output layer. In the case where the descriptor output from the CVAE 520 is used as input data of the DNN 500, a property value may be generated. In the case where the output descriptor is used as input data of the RNN 510, a structure characteristic value may be generated.

Figure 6:
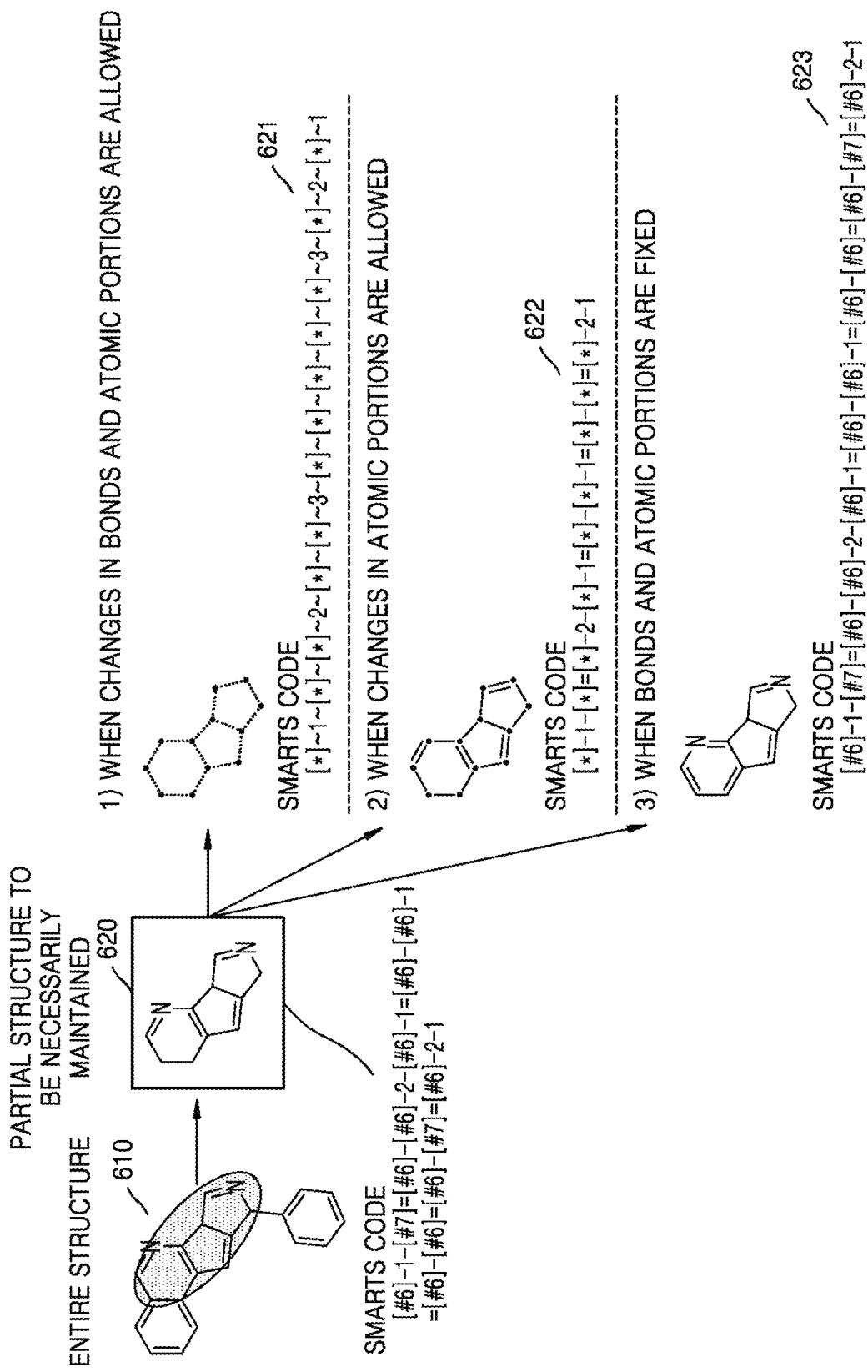
FIG. 6 is a diagram for describing an example of expressing a structural formula of a substance as a character string according to an exemplary embodiment.

FIG. 6 is a diagram for describing an example of expressing a structural formula of a substance as a character string according to an exemplary embodiment.

Referring to FIG. 6, an example of expressing a structural formula of a substance as a character string is illustrated. In the entire structure 610 of a substance, there may be a partial structure 620 to be maintained, i.e., necessarily included in a chemical structure to be finally generated.

The partial structure 620 may be expressed by a character string such as a SMILES code, a SMARTS code, or an InChi code. For example, the partial structure 620 may be expressed as a SMARTS code shown in Expression 6.

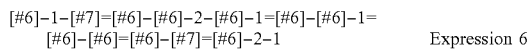

[#6]-1-[#7]=[#6]-[#6]-2-[#6]-1=[#6]-[#6]-1=
[#6]-[#6]=[#6]-[#7]=[#6]-2-1     Expression 6

In addition, when changes in bonds and atomic portions are allowed in the partial structure 620, the partial structure 620 may be expressed as a SMARTS code 621. When changes in atomic portions are allowed in the partial structure 620, the partial structure 620 may be expressed as a SMARTS code 622. When bonds and atomic portions are fixed in the partial structure 620, the partial structure 620 may be expressed as a SMARTS code 623.

Figure 7:
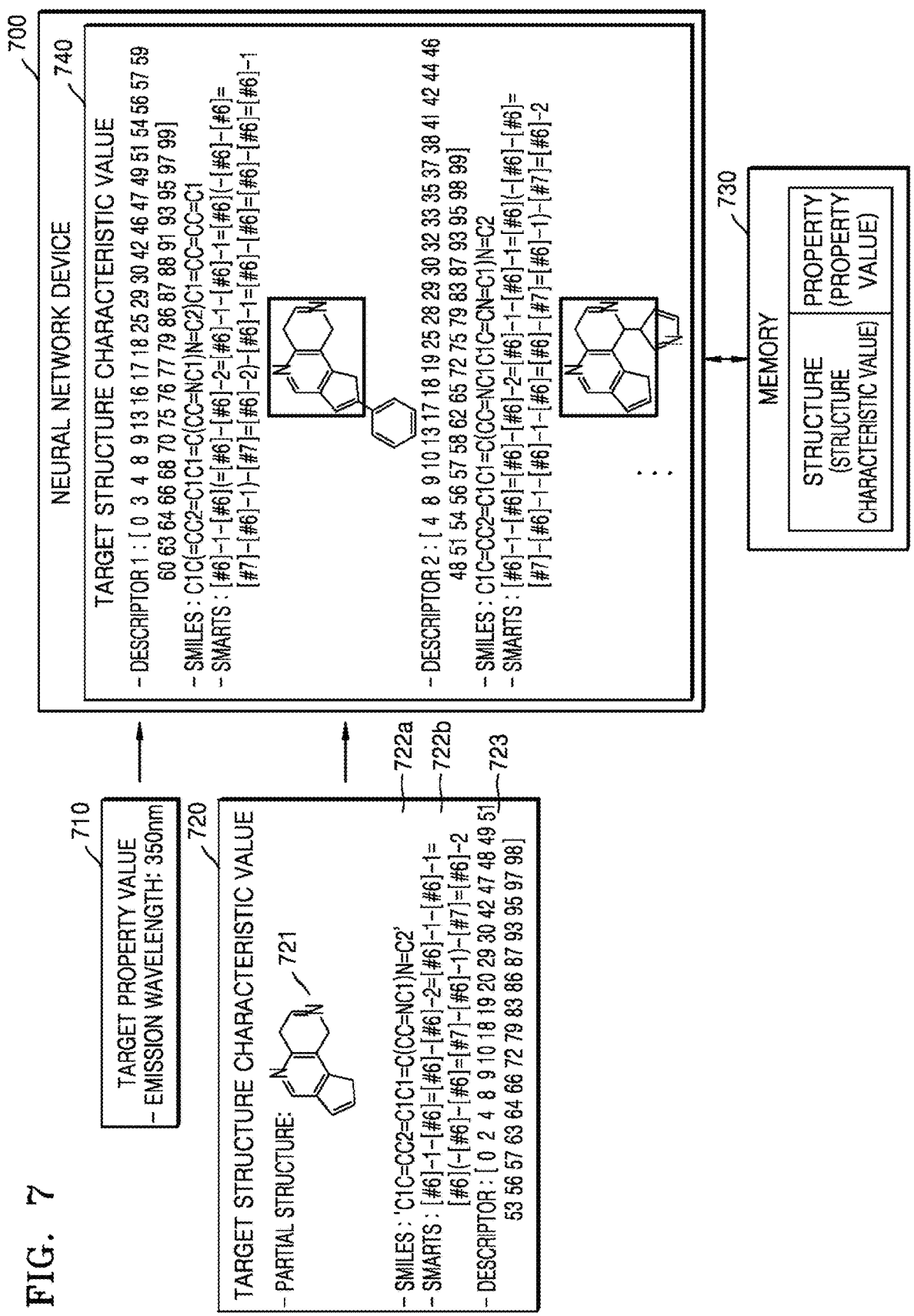
FIG. 7 is a diagram for describing a process of selecting first generation descriptors according to an exemplary embodiment.

FIG. 7 is a diagram for describing a process of selecting first generation descriptors according to an exemplary embodiment.

Referring to FIG. 7, a neural network device 700 may receive a target property value 710 and a target structure characteristic value 720 as input values. The neural network device 700 may generate chemical structures satisfying the target property value 710 and the target structure characteristic value 720. That is, the neural network device may generate a chemical structure including a predetermined partial structure and having improved properties.

The target property value 710 refers to a numerical value of a certain property possessed by a chemical structure that is to be finally generated by the neural network device 700. According to an exemplary embodiment, the target property value 710 may be a refractive index value, an elastic modulus, a melting point, a transmission wavelength, an emission wavelength, and/or the like. For example, the neural network device 700 may receive 'emission wavelength: $\lambda$=350 nm' as the target property value 710.

According to another exemplary embodiment, and instead of including a numerical value, the target property value 710 may include an indicator that identifies that a chemical structure to be finally generated is to include a property value in an increasing (+) direction or a decreasing (−) direction as compared to a predetermined value. A memory 730 stores a structure characteristic value and a property value matching each other as one set. The neural network device 700 may select a given property value stored in the memory 730. In this case, since the neural network device 700 sets the target property value 710 as an indicator identifying that the chemical structure to be finally generated is to include a property value in the increasing direction rather than a certain numerical value, the chemical structure to be finally generated may have a property value greater than the property value selected in the memory 730.

The target structure characteristic value 720 refers to a numerical value of a partial structure included in a chemical structure to be finally generated by the neural network device 700. The partial structure may be expressed, for example, as a SMILES code or SMARTS code. In addition, in order to express the partial structure expressed as a SMILES code or SMARTS code with a numerical value, a descriptor such as ECFP and QSPR may be used.

According to an exemplary embodiment, the target structure characteristic value 720 may be a descriptor of a particular chemical structure. For example, the partial structure 721 may be expressed as a SMILES code 722a or a SMARTS code 722b. The neural network device 700 may receive a descriptor 723 corresponding to the SMILES code 722a or the SMARTS code 722b as the target structure characteristic value 720. FIG. 7 illustrates the SMILES code and the SMARTS code, and the chemical structure corresponding to the descriptor 723 for ease of understanding.

Meanwhile, the descriptor may be a binary value having a length of 100 bits. Hereinafter, the descriptor will be expressed only by digits having a bit value of "1" for descriptive convenience. For example, the descriptor 723 may be expressed by [0 2 4 8 9 10 18 19 20 29 30 42 47 48 49 51 53 56 57 63 64 66 72 79 83 86 87 93 95 97 98]. In this case, the digits 0, 2, 4, 8, 9, 10, and the like of the descriptor 723 indicate the bit value "1" and the digits 1, 3, 5, 6, 7, 11, and the like indicate the bit value "0".

The neural network device 700 may select first generation descriptors 740 based on the received target property value 710 and the target structure characteristic value 720. Particularly, the neural network device 700 may select first generation descriptors 740 having a property value similar to the received target property value 710 (e.g., that satisfies a threshold similarity value) and a structure characteristic value similar to the received target structure characteristic value 720 (e.g., that satisfies a threshold similarity value) from the memory 730 in which structure characteristic values and property values matching each other are stored.

Referring to FIG. 7, the neural network device 700 receives an input of 'emission wavelength: $\lambda$=350 nm' as the target property value 710 and an input of the descriptor 723 as the target structure characteristic value 720. The neural network device 700 may select chemical structures having a structure characteristic value and a property value similar to the received inputs from the memory 730. The selected chemical structures may have the target structure characteristic value 740 expressed as Descriptors 1 and 2, and a plurality of descriptors (e.g., Descriptors 1 and 2) included in the target structure characteristic value 740 correspond to the first generation descriptors. Meanwhile, FIG. 7 illustrates SMILES codes, SMARTS codes, and chemical structures corresponding respectively to Descriptors 1 and 2 for ease of understanding.

FIG. 8 is a diagram for describing a process of applying a genetic algorithm to the first generation descriptors according to an exemplary embodiment.

Referring to FIG. 8, a neural network device may generate second generation descriptors by applying a genetic algorithm to the first generation descriptors. Genetic algorithms are algorithms used to generate new candidate substances by performing crossover and mutation operations on previous candidate substances. The operations of the genetic algorithm might include arbitrary processes. The genetic algorithm includes operations such as selection, crossover, mutation, and/or the like. Selection is a process to select candidate substances that are passed on from one generation to a next generation. Crossover is a process of generating candidate substances of a next generation via mating within one generation. Mutation is a process of changing candidate substances via a random change in the order or value of the descriptor in one candidate substance.

Referring to FIG. 8, the neural network device may select the first generation descriptors. The first generation descriptors are Descriptors 1 to 4, and Descriptors 1 to 4 may be expressed by binary codes.

The neural network device may perform crossover and mutation operations on Descriptors 1 to 4 selected as the first generation descriptors. As a result of crossover and mutation operations, the neural network device may generate second generation descriptors from the first generation descriptors (Descriptors 1 to 4).

Figure 9A:
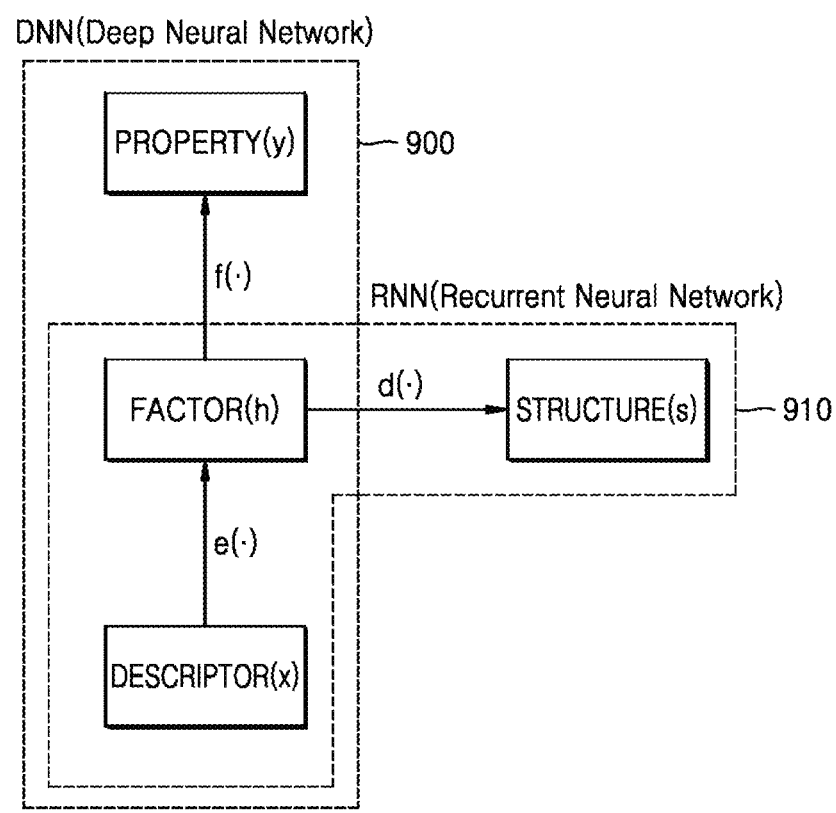
FIGS. 9A and 9B are diagrams for describing a process of evaluating properties and structures of descriptors according to an exemplary embodiment.
Figure 9B:
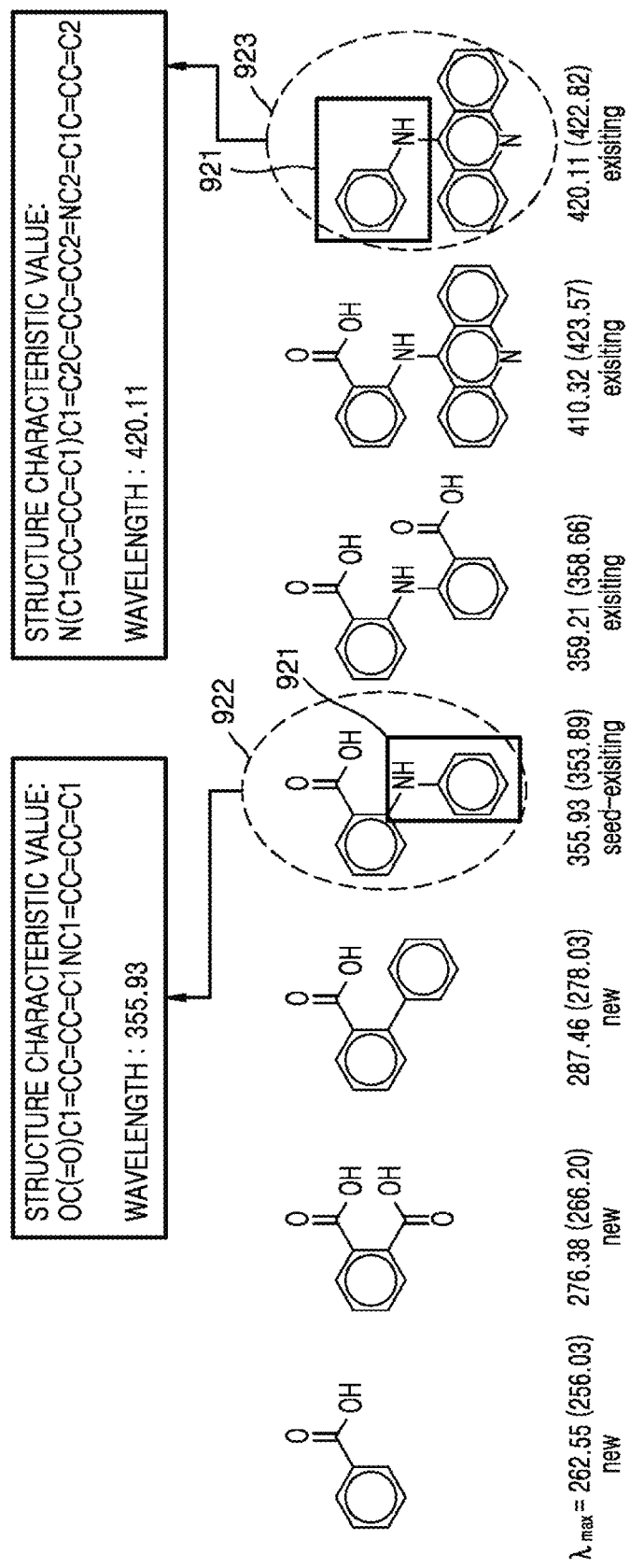

FIGS. 9A and 9B are diagrams for describing a process of evaluating properties and structures of descriptors according to an exemplary embodiment.

Referring to FIG. 9A, a DNN 900 of the neural network device is a neural network in which a factor defining the relationship between a descriptor and a property is determined via learning using descriptors and properties (property values).

Particularly, the DNN 900 learns an encoding function e(•) and a prediction function f(•) based on (x, y) data that indicates a descriptor and a property value, and/or other information. The encoding function e(•) is a function for deriving hidden parameters from the descriptor. When the descriptor is x, a factor h(=e(x)) with respect to the descriptor x may be determined via the encoding function. The prediction function f(•) is a function for predicting a property based on the factor acquired based on the encoding.

When the factor h is substituted into the prediction function, a property y (=f(h)) with respect to the factor h may be determined via the prediction function. In the learning operation, the DNN 900 may determine the factor such that a probability of data (x, y) is maximized or a difference between a property value f(e(x)) via prediction and a real property y is minimized.

The DNN 900 performs a computation using the descriptor as input data to the input layer and generates the property value as output data based on a computation result. The factor may be an undisclosed core element to represent the relationship between the descriptor and the property. Among a plurality of layers constituting the DNN 900, the descriptor may be an input layer, the factor may be a hidden layer, and the property value may be an output layer.

The neural network device inputs second generation descriptors to the DNN 900 as input data and generates property values of the respective second generation descriptors as output data by applying the encoding function e(•) and the prediction function f(•) thereto. The neural network device may evaluate the properties of the second generation descriptors by comparing the generated property values with a target property value.

In addition, an RNN 910 of the neural network device is a neural network in which a factor defining the relationship between a descriptor and a structure is determined via learning using descriptors and structures (structure characteristic values).

Particularly, the RNN 910 learns the encoding function e(•) and a decoding function d(•) based on (x, s) data that indicates a descriptor and a structure characteristic value, and the factor may be determined in the process of learning the decoding function d(•) Meanwhile, when the encoding function e(•) is determined via the learning process of the DNN 900, the RNN 910 may learn the decoding function d(•) based on (h, s) data that includes a factor and a structure characteristic value by using the encoding function e(•) determined by the DNN 900.

The decoding function d(•) is a function to generate a structure of a substance at the atomic level by using the factor derived from the descriptor. When the structure is expressed as s, s=d(h) is established.

The RNN 910 performs a computation using the descriptor as input data to the input layer and generates the structure characteristic value as output data based on a computation result. The factor may be an undisclosed core element to represent the relationship between the descriptor and the structure and may be a hidden layer of the RNN 910. The hidden layer generated via the learning process of the DNN 900 may also be used.

The neural network device inputs second generation descriptors to the RNN 910 as input data and generates structure characteristic values of the respective second generation descriptors as output data by applying the encoding function e(•) and the decoding function d(•) thereto. The neural network device may evaluate structures of the second generation descriptors by identifying whether or not the generated structure characteristic values include the target structure characteristic value.

Particularly, the RNN 910 may generate the structure characteristic value (final chemical structure) in the form of SMILES code. When the target structure characteristic value (partial structure) is input in the form of SMARTS code, the neural network device may determine whether or not the structure characteristic value includes the target structure characteristic value by comparing a SMILES code corresponding to the structure characteristic value with a SMARTS code corresponding to the target structure characteristic value by using an RDkit library. When the structure characteristic value generated by the RNN 910 includes the target structure characteristic value, i.e., when the generated final chemical structure includes a partial structure, the neural network device may select the second generation descriptor input to the RNN 910 as a candidate descriptor. Meanwhile, methods of expressing the structure characteristic values (final chemical structures) and the target structures characteristic values (partial structures) are not limited thereto.

The neural network device may evaluate the properties of the second generation descriptors by using the DNN 900 and the structures of the second generation descriptors by using the RNN 910. In addition, the neural network device may select candidate descriptors having the target property value and the target structure characteristic value from the second generation descriptors based on the evaluation results of the properties and structures. Finally, the neural network device generates chemical structures for the selected candidate descriptors, thereby generating improved chemical structures including the particular partial structure and having the target property value.

Meanwhile, when the property values and/or structure characteristic values of the second generation descriptors do not satisfy the target values, the neural network device may generate third generation descriptors by applying the genetic algorithm to the second generation descriptors. The neural network device may evaluate properties of the third generation descriptors by using the DNN 900 and structures of the third generation descriptors by using the RNN 910. The neural network device may modify (e.g., evolve) the descriptors by using the genetic algorithm until descriptors satisfying the target property value and the target structure characteristic value are generated. In other words, the neural network device may iteratively generate descriptors, and evaluate properties and structures of the generated descriptors based on whether the generated descriptors satisfy the target property value and the target structure characteristic value.

In addition, when the number of candidate descriptors having the target property value and the target structure characteristic value is less than a preset value as a result of evaluation of the properties and structures of the second generation descriptors, the neural network device may change a transformation index applied to the genetic algorithm.

Meanwhile, the degree of transformation of the first generation descriptors may vary according to the transformation index applied to the genetic algorithm. According to an exemplary embodiment, lowering the transformation index may refer to lowering the number of operations with large degrees of transformation of the first generation descriptors, among selection, crossover, mutation, and replace operations constituting the genetic algorithm. However, methods of changing the transformation index are not limited thereto.

The neural network device may re-generate second generation descriptors from the first generation descriptors after changing the transformation index of the genetic algorithm. According to an exemplary embodiment, and as an example, when 100 second generation descriptors are generated and the number of descriptors having the target property value and the target structure characteristic value is 10 or less, the neural network device may lower the transformation index of the genetic algorithm and then apply the genetic algorithm to the first generation descriptors again to re-generate the second generation descriptors.

Referring to FIG. 9B, the neural network device may generate chemical structures including a particular partial structure and having improved properties by evolving the descriptors by using the genetic algorithm and evaluating property values and structure characteristic values of the generated descriptors by using the DNN 900 and the RNN 910.

According to an exemplary embodiment, the neural network device may gradually generate chemical structures including the particular partial structure and having improved properties. For example, the neural network device may generate a chemical structure including a partial structure 921 and an increased wavelength (T1 value).

Particularly, the neural network device may select a chemical structure 922 including the partial structure 921, having a T1 value of 355.93, and a structure characteristic value of 'OC(=O)C1=CC=CC=C1NC1=CC=CC=C1'. The neural network device may generate a chemical structure 923 including the partial structure 921 and having an increased T1 value of 420.11 by applying the genetic algorithm to the structure characteristic value 'OC(=O)C1=CC=CC=C1NC1=CC=CC=C1' of the selected chemical structure 922. The generated chemical structure 923 has a structure characteristic value of 'N(C1=CC=CC=C1)C1=C2C=CC=CC2=NC2=C1C=CC=C2'.

In this way, the neural network device may generate a chemical structure including the partial structure 921 and having an increased T1 value by applying the genetic algorithm to the generated chemical structure 923. The neural network device may generate chemical structures by applying the genetic algorithm thereto until a chemical structure having a property value similar to the target property value is generated (e.g., that satisfies a threshold similarity value, that satisfies the target property value, that is within a threshold range of the target property value, that satisfies a predetermined metric, and/or the like).

According to another exemplary embodiment, the neural network device may also generate a chemical structure including a particular partial structure and a reduced T1 value by applying the genetic algorithm to the generated chemical structure 923.

Figure 10:
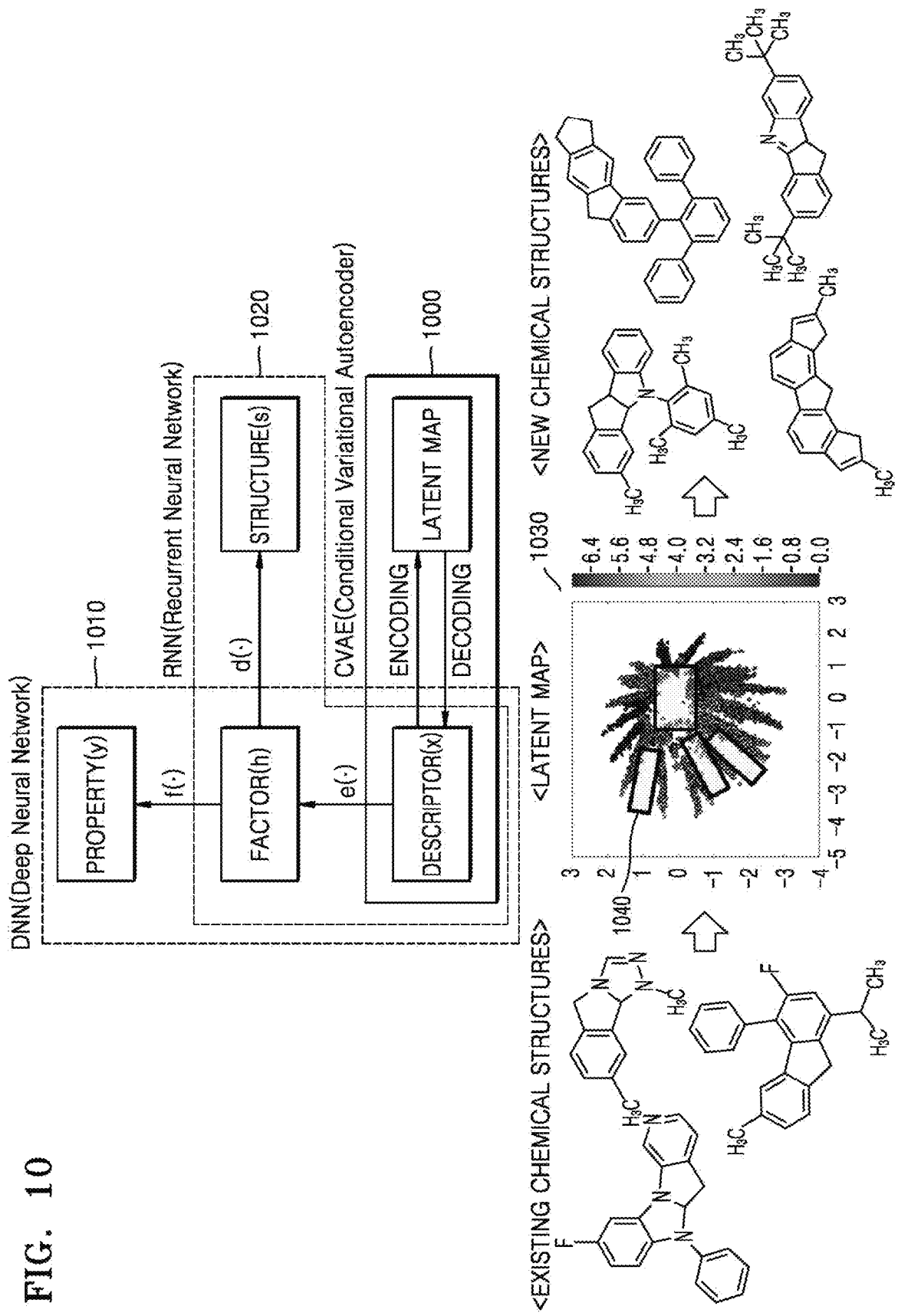
FIG. 10 is a conceptual diagram of a neural network system configured to generate a chemical structure by using the CVAE according to an exemplary embodiment.

FIG. 10 is a conceptual diagram of a neural network system configured to generate a chemical structure by using a CVAE according to an exemplary embodiment.

A CVAE 1000 of the neural network device uses a descriptor that is high-dimensional data stored in the database as input data to an input layer, and encoding by converting the high-dimensional descriptor into a latent variable that is low-dimensional data is performed by an encoder. Next, a decoder of the CVAE 1000 decodes the low-dimensional latent variable, and finally, a descriptor that is high-dimensional data corresponding to a new chemical structure is output from an output layer.

Particularly, the CVAE 1000 may encode a high-dimensional descriptor x for each of the existing chemical structures into a low-dimensional latent variable I. The latent variable I may include a two-dimensional descriptor z obtained by lowering a dimension of the high-dimensional descriptor x and core structure information t. However, data included in the latent variable I is not limited thereto.

Examples of structures corresponding to the core structure information t are shown in Table 1 below.

TABLE 1

| Core structure information t | Core structure |
|---|---|
| t = 0 | |
| t = 1 | |
| t = 2 | |
| t = 3 | |
| t = 4 | |
| t = 5 | |
| t = 6 | |
| t = 7 | |

The latent variable I may be mapped to a latent map 1030. The two-dimensional descriptor z included in the latent variable I corresponds to (x, y) coordinate values of the latent map 1030 and the core structure information t included in the latent variable I is distinguished by colors in the latent map 1030 (where colors of the latent map 1030 are not shown in FIG. 10).

According to an exemplary embodiment, core structure information t may be shown in eight different colors in the latent map 1030. For example, a latent variable I having a core structure t=0 may be shown in a first color (e.g., blue) in the latent map 1030 and a latent variable I having a core structure t=1 may be shown in a second color (e.g., sky blue) in the latent map 1030.

When the latent map 1030 is used, similarity between the descriptors may be visually identified. In the latent map 1030, it may be confirmed that the descriptors are gathered according to the structure form. Thus, a new chemical structure including a particular structural form may be generated thereby. Referring to the latent map 1030 of FIG. 10, it may be confirmed that the descriptors are gathered by the same color, i.e., the same structural form.

The CVAE 1000 may select a region 1040 to which latent variables are not mapped from the latent map 1030. When latent variables of the selected region 1040 are decoded, the latent variables may be converted into high-dimensional descriptors. The CVAE 1000 may generate chemical structures for the converted high-dimensional descriptors, thereby creating new chemical structures.

That is, the CVAE 1000 may generate new chemical structures not stored in the database by decoding predetermined latent variables of the region 1040 of the latent map 1030 to which the latent variables are not mapped. Also, chemical structures including the particular structure may be generated by decoding latent variables of a region of the latent map 1030 adjacent to a region in which latent variables of the particular structure are gathered.

In addition, the neural network device may generate property values of the new chemical structures generated by the CVAE 1000 by using a DNN 1010 and structure characteristic values thereof by using an RNN 1020. The neural network device may also evaluate properties and structural characteristics of the new chemical structures. When the target property value and the target structure characteristic value are not satisfied as a result of evaluation, the neural network device generates next generation chemical structures by applying the genetic algorithm to the generated new chemical structures.

Figure 11:
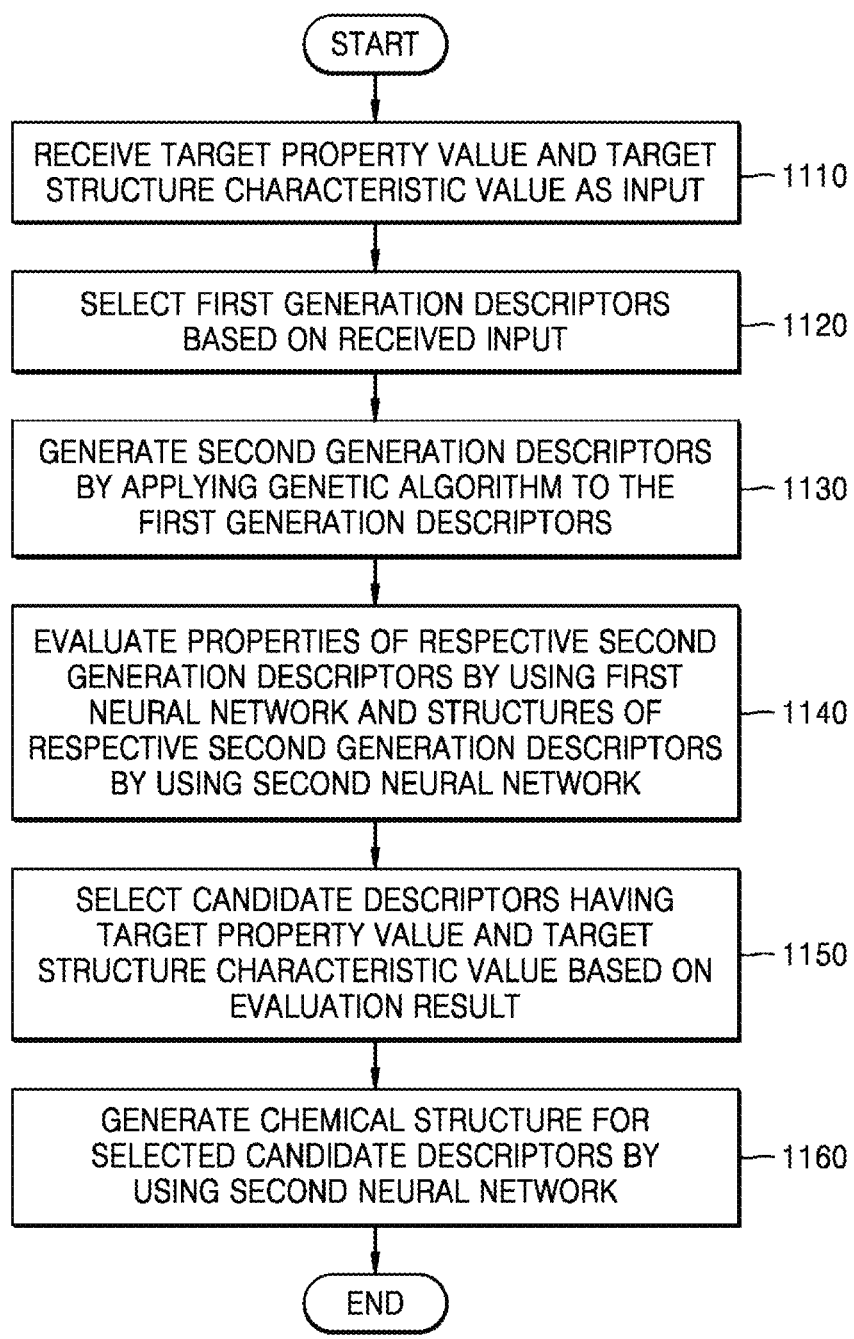
FIG. 11 is a flowchart for describing a method of generating a chemical structure by using the DNN and the RNN according to an exemplary embodiment.

FIG. 11 is a flowchart for describing a method of generating a chemical structure by using a DNN and an RNN according to an exemplary embodiment. The method of generating a chemical structure performed by the neural network device illustrated in FIG. 11 is related to the exemplary embodiments described above with reference to the drawings. Thus, although omitted in the following descriptions, the contents described above with reference to the drawings may also be applied to the method illustrated in FIG. 11.

Referring to FIG. 11, the neural network device may receive a target property value and a target structure characteristic value as input data in operation 1110.

The target property value may be indicative of a certain property possessed by a chemical structure to be finally generated by the neural network device. The target property value may be a numerical value, a range of numerical values, or the like. According to an exemplary embodiment, the target property value may be, for example, a refractive index value, an elastic modulus, a melting point, a transmission wavelength, an emission wavelength, and/or the like. According to another exemplary embodiment, and instead of including a given numerical value, the target property value 710 may be set as an indicator identifying that a chemical structure to be finally generated is to include a property value in an increasing (+) direction or a decreasing (−) direction as compared to a predetermined value.

The target structure characteristic value may be indicative of a partial structure included in a chemical structure to be finally generated by the neural network device. A descriptor such as ECFP and QSPR may be used to express the partial structure with a numerical value.

The neural network device may generate a chemical structure including the particular partial structure and having an improved property based on the target property value and the target structure characteristic value.

In operation 1120, the neural network device may select first generation descriptors based on the received input data. The neural network device may select descriptors having a property value similar to the received target property value and a structure characteristic value similar to the received target structure characteristic value as the first generation descriptors among the descriptors stored in the memory.

The neural network device may determine a descriptor that includes a property value that satisfies a threshold similarity value to the received target property value. For example, the property value may be within a threshold range of the target property value, may be greater than the target property value, and/or the like. The neural network device may select the descriptor based on the descriptor including a property value that satisfies the threshold similarity value.

The neural network device may determine a descriptor that includes a structure characteristic value that satisfies a threshold similarity value to the target structure characteristic value. For example, the structure characteristic value may satisfy a particular metric, may be within a threshold range of the target structure characteristic value, may match the target structure characteristic value, and/or the like. The neural network device may select the descriptor based on the descriptor including a structure characteristic value that satisfies the threshold similarity value.

In operation 1130, the neural network device may generate second generation descriptors by applying the genetic algorithm to the first generation descriptors. The neural network device may generate the second generation descriptors by performing crossover and mutation operations on the first generation descriptors.

In operation 1140, the neural network device may evaluate properties and structures of the second generation descriptors.

The neural network device may generate property values of the respective second generation descriptors as output data by inputting second generation descriptors to the DNN as input data and applying the encoding function and the prediction function thereto. The neural network device may evaluate the properties of the second generation descriptors by comparing the generated property values with the target property value.

Also, the neural network device may generate structure characteristic values of the respective second generation descriptors as output data by inputting second generation descriptors to the RNN as input data and applying the encoding function and the decoding function thereto. The neural network device may evaluate structures of the second generation descriptors by comparing the generated structure characteristic values with the target structure characteristic value.

According to an exemplary embodiment, the neural network device may determine whether or not the structure characteristic values include a target structure characteristic value by comparing a SMILES code corresponding to the structure characteristic value with a SMARTS code corresponding to the target structure characteristic value by using the RDkit library. When the structure characteristic values generated by the RNN include the target structure characteristic value, i.e., when the generated final chemical structures include the partial structure, the neural network device may select the second generation descriptors input to the RNN as candidate descriptors.

In operation 1150, the neural network device may select candidate descriptors satisfying the target property value and the target structure characteristic value from the second generation descriptors based on the evaluation result.

Meanwhile, when the property values and/or the structure characteristic values of the second generation descriptors do not satisfy the target values, the neural network device may generate third generation descriptors by applying the genetic algorithm to the second generation descriptors. The neural network device may evaluate properties of the third generation descriptors by using the DNN and structures of the third generation descriptors by using the RNN. That is, the neural network device may evolve the descriptors by using the genetic algorithm until descriptors satisfying the target property value and the target structure characteristic value are generated. In other words, the neural network device may iteratively evolve the descriptors until the generated descriptors satisfy the target property value and the target characteristic value.

In operation 1160, the neural network device may generate chemical structures for the selected candidate descriptors.

The neural network device may generate structure characteristic values of the respective candidate descriptors as output data by inputting the candidate descriptors to the RNN as input data and applying the encoding function and the decoding function thereto. The neural network device may generate chemical structures by converting the generated structure characteristic values into a SMILES code, an InChi code, or the like.

Figure 12:
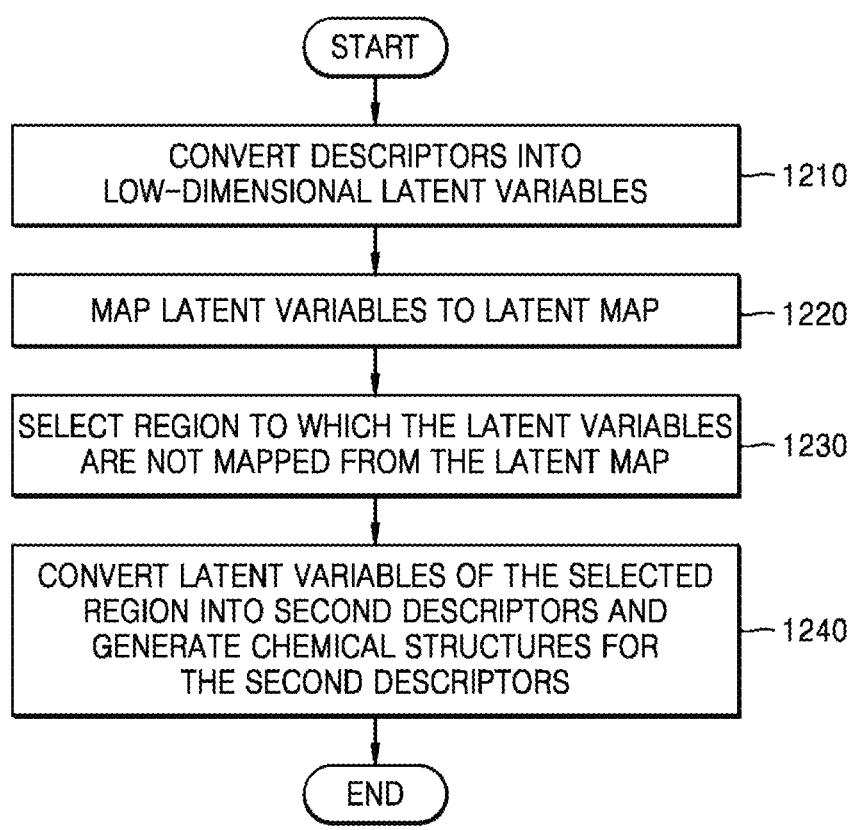
FIG. 12 is a flowchart for describing a method of generating a chemical structure by using the CVAE according to an exemplary embodiment.

FIG. 12 is a flowchart for describing a method of generating a chemical structure by using a CVAE according to an exemplary embodiment. The method of generating a chemical structure performed by the neural network device illustrated in FIG. 12 is related to the exemplary embodiments described above with reference to the drawings. Thus, although omitted in the following descriptions, the contents described above with reference to the drawings may also be applied to the method illustrated in FIG. 12.

Referring to FIG. 12, the neural network device may convert first descriptors into low-dimensional latent variables in operation 1210.

Since the memory stores a structure (structure characteristic value) and a property (property value) matching each other as one set. Since the structure characteristic value is stored in the memory in the form of descriptor and the descriptor stored in the memory may be high-dimensional data.

The neural network device may convert the descriptors (i.e., first descriptors) of the chemical structures stored in the memory to low-dimensional latent variables respectively. According to an exemplary embodiment, after receiving a target property value and/or a target structure characteristic value as input data, the neural network device may select some of the descriptor of the chemical structures stored in the memory as the first descriptors based on the received input. The neural network device may convert the selected first descriptors into low-dimensional latent variables.

The neural network device may encode high-dimensional descriptors into low-dimensional latent variables I by using the CVAE. The latent variables may include two-dimensional descriptors obtained by lowering dimension of the high-dimensional descriptors and core structures.

In operation 1220, the neural network device may map the latent variables to the latent map.

The two-dimensional descriptors included in the latent variables may correspond to (x, y) coordinate values of the latent map and the core structures t included in the latent variables may be expressed as colors in the latent map.

In operation 1230, the neural network device may select a region to which latent variables are not mapped from the latent map.

The neural network device may input predetermined values included in the region of the latent map to which the latent variables are not mapped to the decoder and decode the predetermined value, thereby generating new chemical structures not stored in the database.

Since it may be confirmed that the descriptors are gathered according to the structure form in the latent map, a new chemical structure may be generated thereby. Chemical structures including the particular structure may be generated by decoding latent variables of a region adjacent to a region in which latent variables of the particular structure are gathered among the latent variables included in the regions to which the latent variables of the existing chemical structures are not mapped.

In operation 1240, the neural network device may convert the latent variables of the selected region into high-dimensional second descriptors and generate chemical structures for the second descriptors.

The neural network device may convert the latent variables into the high-dimensional descriptors by decoding the latent variables of the selected region by using the CVAE. Also, the neural network device may generate new chemical structures by generating chemical structures for the converted high-dimensional descriptors by using the CVAE.

In addition, the neural network device may evaluate properties and structures of the respective converted high-dimensional descriptors. When the target property value and the target structure characteristic value are not satisfied as a result of evaluation, the neural network device may generate next generation chemical structures by applying the genetic algorithm to the converted high-dimensional descriptors. Descriptions thereof are similar as those of operations 1110 to 1160 of FIG. 11.

Also, the aforementioned exemplary embodiments may be embodied in the form of a recording medium including instructions executable by a computer, such as a program module, executed by a computer. The computer-readable medium may be any recording medium that may be accessed by a computer and may include volatile and non-volatile media and removable and non-removable media. The computer-readable medium may include a non-transitory computer-readable medium that stores one or more instructions that, when executed by one or more processors, cause the one or more processors to perform operations associated with exemplary embodiments described herein. Also, the computer-readable medium may include computer storage media and communication media. The computer storage media include volatile and non-volatile and removable and non-removable media implemented using any method or technology to store information such as computer-readable instructions, data structures, program modules, or other data. The communication media include computer-readable instructions, data structures, program modules, or other data in a modulated data signal, or other transport mechanisms and include any delivery media.

In addition, throughout the specification, the term "unit" may be a hardware component such as a processor or a circuit and/or a software component executed by the hardware component such as a processor.

The above description of the present disclosure is provided for the purpose of illustration, and it should be understood by those skilled in the art that various changes and modifications may be made without changing technical conception and essential features of the present disclosure. Thus, it is clear that the above-described illustrative exemplary embodiments are illustrative in all aspects and do not limit the present disclosure. For example, each component described to be of a single type may be implemented in a distributed manner. Likewise, components described to be distributed may be implemented in a combined manner.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of generating a chemical structure, the method being performed by a neural network device and comprising:
   receiving a target property value and a target structure characteristic value as separate inputs;
   selecting first generation descriptors based on the target property value and the target structure characteristic value;
   generating second generation descriptors based on the first generation descriptors;
   determining, using a first neural network of the neural network device, property values of the second generation descriptors;
   determining, using a second neural network of the neural network device, structure characteristic values of the second generation descriptors;
   selecting, from the second generation descriptors, candidate descriptors that satisfy the target property value and the target structure characteristic value, the selecting of the candidate descriptors being based on the determining the property values and based on the determining the structure characteristic values; and
   generating, using the second neural network of the neural network device, chemical structures for the selected candidate descriptors.

2. The method of claim 1, further comprising:
   changing a transformation index that is used to generate the second generation descriptors, the changing being based on a number of the selected candidate descriptors being less than a predetermined value; and
   re-generating second generation descriptors based on the changed transformation index.

3. The method of claim 1, further comprising:
   inputting the second generation descriptors to the first neural network, which is a deep neural network (DNN), and generating the property values of the second generation descriptors; and
   comparing the generated property values with the target property value.

4. The method of claim 1, further comprising:
   inputting the second generation descriptors to the second neural network, which is a recurrent neural network (RNN), and generating the structure characteristic values of the second generation descriptors; and
   determining whether the generated structure characteristic values comprise the target structure characteristic value.

5. A non-transitory computer-readable recording medium comprising a program, which when executed by one or more processors, causes the one or more processors to perform the method of claim 1.

6. A neural network device configured to generate a chemical structure, the neural network device comprising:
   a user interface configured to receive a target property value and a target structure characteristic value as separate inputs;
   a memory configured to store at least one program; and
   a processor configured to execute the at least one program to:
   select first generation descriptors based on the target property value and the target structure characteristic value;
   generate second generation descriptors based on the first generation descriptors;
   determine, using a first neural network, property values of the second generation descriptors;
   determine, using a second neural network, structure characteristic values of the second generation descriptors;
   select, from the second generation descriptors, candidate descriptors that satisfy the target property value and the target structure characteristic value, based on determining the property values and the structure characteristic values; and
   generate, using the second neural network, chemical structures for the selected candidate descriptors.

7. The neural network device of claim 6, wherein the processor is further configured to change a transformation index that is used to generate the second generation descriptors, based on a number of the selected candidate descriptors being less than a predetermined value; and
   re-generate the second generation descriptors based on the changed transformation index.

8. The neural network device of claim 6, wherein the processor is further configured to input the second generation descriptors to the first neural network and generate the property values of the second generation descriptors; and
   compare the generated property values with the target property value,
   wherein the first neural network is a deep neural network (DNN).

9. The neural network device of claim 6, wherein the processor is further configured to input the second generation descriptors to the second neural network and generate the structure characteristic values of the second generation descriptors; and
   determine whether the generated structure characteristic values comprise the target structure characteristic value,
   wherein the second neural network is a recurrent neural network (RNN).

10. A method of generating a chemical structure by using a conditional variational autoencoder (CVAE) of a neural network device, the method comprising:
    receiving a target property value and a target structure characteristic value as separate inputs;
    converting first descriptors into low-dimensional latent variables;
    mapping the low-dimensional latent variables to a latent map;
    selecting, using the latent map, a region to which the low-dimensional latent variables that are converted from the first descriptors are not mapped;
    converting latent variables of the selected region into high-dimensional second descriptors based on the first descriptors;
    selecting, from the high-dimensional second descriptors, candidate descriptors that satisfy the target property value and the target structure characteristic value;

determining, by applying the high-dimensional second descriptors to a first neural network, property values of the high-dimensional second descriptors;

determining, by applying the high-dimensional second descriptors to a second neural network, structure characteristic values of the high-dimensional second descriptors; and generating chemical structures for the high-dimensional second descriptors.

11. The method of claim 10, wherein the low-dimensional latent variables comprise core structure information and a low-dimensional descriptor.

12. The method of claim 10,
wherein the selecting of the candidate descriptors being based on determining the property values and the structure characteristic values; and wherein the method further comprising generating, using the second neural network, the chemical structures for the selected candidate descriptors.

13. The method of claim 12, further comprising:
inputting the high-dimensional second descriptors to the first neural network and generating the property values of the high-dimensional second descriptors; and comparing the generated property values with the target property value, wherein the first neural network is a deep neural network (DNN).

14. The method of claim 12, further comprising:
inputting the high-dimensional second descriptors to the second neural network and generating chemical structure values of the high-dimensional second descriptors; and determining whether the generated chemical structure values comprise the target structure characteristic value, wherein the second neural network is a recurrent neural network (RNN).

15. The method of claim 10, further comprising:
generating next generation descriptors based on the high-dimensional second descriptors;

determining, using the first neural network, the property values of the next generation descriptors;

selecting, from the next generation descriptors, the candidate descriptors that satisfy the target property value; and generating, using the neural network, the chemical structures for the selected candidate descriptors.

16. A neural network device configured to generate a chemical structure by using a conditional variational auto-encoder (CVAE), the neural network device comprising:
a memory configured to store at least one program; and
a processor configured to execute the at least one program to:
receive a target property value and a target structure characteristic value as separate inputs;
convert first descriptors into low-dimensional latent variables;
map the low-dimensional latent variables to a latent map;
select, using the map, a region to which the low-dimensional latent variables converted from the first descriptors are not mapped;
convert latent variables of the selected region into high-dimensional second descriptors based on the first descriptors;

select, from the high-dimensional second descriptors, candidate descriptors that satisfy the target property value and the target structure characteristic value;

determine, by applying the high-dimensional second descriptors to a first neural network, property values of the high-dimensional second descriptors;

determine, by applying the high-dimensional second descriptors to a second neural network, structure characteristic values of the high-dimensional second descriptors; and generate chemical structures for the high-dimensional second descriptors.

17. The neural network device of claim 16, wherein the low-dimensional latent variables comprise core structure information and a low-dimensional descriptor.

18. The neural network device of claim 16, further comprising a user interface configured to receive the target property value and the target structure characteristic value; and wherein the processor is further configured to:
select, from the high-dimensional second descriptors, the candidate descriptors that satisfy the target property value and the target structure characteristic value, based on determining the property values and the structure characteristic values; and generate, using the second neural network, the chemical structures for the selected candidate descriptors.

19. The neural network device of claim 18, wherein the processor is further configured to input the high-dimensional second descriptors to a recurrent neural network and generate chemical structures for high-dimensional second descriptors, and determine whether the generated chemical structures comprise the target structure characteristic value.

20. The neural network device of claim 18, wherein the processor is further configured to input the high-dimensional second descriptors to a deep neural network and generate the property values of the high-dimensional second descriptors, and compare the generated property values with the target property value.

21. The neural network device of claim 16, further comprising a user interface configured to receive the target property value and the target structure characteristic value; and wherein the processor is further configured to:
generate next generation descriptors based on the high-dimensional second descriptors;
determine, using the first neural network, the property values of the next generation descriptors;
determine, using the second neural network, structure characteristic values of the next generation descriptors;
select, from the next generation descriptors, the candidate descriptors that satisfy the target property value and the target structure characteristic value, based on determining the property values and the structure characteristic values; and
generate, using the second neural network, the chemical structures for the selected candidate descriptors.

22. A method, comprising:
receiving, by a device, first information that identifies a target property value and second information that identifies a target structure characteristic value of a substance as separate inputs;

determining, by the device, a first set of descriptors based on the information that identifies the target property value and the target structure characteristic value of the substance;

generating, by the device, a second set of descriptors that is different than the first set of descriptors, the generating being based on determining the first set of descriptors;

determining, by the device and using a first neural network of the device, property values of the second set of descriptors;

determining, by the device and using a second neural network that is different than the first neural network, structure characteristic values of the second set of descriptors;

determining, by the device and using the second set of descriptors, a descriptor that satisfies the target property value and the target structure characteristic value, the determining of the descriptor being based on determining the property values and the structure characteristic values; and generating, by the device and using the second neural network of the device, a chemical structure for the descriptor.

23. The method of claim 22, wherein the determining the descriptor that satisfies the target property value and the target structure characteristic value comprises:

comparing the target property value and the generated property values of the second descriptors; and determining the descriptor that satisfies the target property value and the target structure characteristic value based on comparing the target property value and the generated property values.

24. The method of claim 22, wherein the determining the descriptor that satisfies the target property value and the target structure characteristic value comprises:

determining that a generated structure characteristic value of the descriptor includes the target structure characteristic value; and determining the descriptor that satisfies the target property value and the target structure characteristic value based on determining that the generated structure characteristic value of the descriptor includes the target structure characteristic value.

25. The method of claim 22, wherein the generating the second set of descriptors comprises:

performing at least one of a selection operation, a crossover operation, and a mutation operation using the first set of descriptors; and generating the second set of descriptors based on performing the at least one of the selection operation, the crossover operation, and the mutation operation using the first set of descriptors.

26. The method of claim 22, wherein the first neural network is a deep neural network, and the second neural network is a recurrent neural network.

* * * * *